US006193972B1

(12) United States Patent
Campbell et al.

(10) Patent No.: US 6,193,972 B1
(45) Date of Patent: Feb. 27, 2001

(54) HYBRID HETERODIMERIC PROTEIN HORMONE

(75) Inventors: Robert K. Campbell, Wrentham; Bradford A. Jameson; Scott C. Chappel, both of Milton, all of MA (US)

(73) Assignee: Applied Research Systems ARS Holding N.V., Netherlands (AN)

( * ) Notice: Subject to any disclaimer, the term of this patent is extended or adjusted under 35 U.S.C. 154(b) by 0 days.

(21) Appl. No.: 08/804,166

(22) Filed: Feb. 20, 1997

Related U.S. Application Data

(60) Provisional application No. 60/011,936, filed on Feb. 20, 1996.

(51) Int. Cl.$^7$ .................................................. C07K 19/00
(52) U.S. Cl. ................................... 424/192.1; 424/193.1; 424/198.1; 435/69.7; 530/350; 530/351; 530/398; 530/399; 935/10
(58) Field of Search ................. 435/69.7; 424/192.1, 424/193.1, 198.1; 530/350, 351, 398, 399; 935/10

(56) References Cited

U.S. PATENT DOCUMENTS

| | | | | |
|---|---|---|---|---|
| 5,116,964 | * | 5/1992 | Capon et al. | 435/69.7 |
| 5,155,027 | * | 10/1992 | Sledziewski et al. | 435/69.7 |
| 5,447,851 | * | 9/1995 | Beutler et al. | 435/69.7 |
| 5,567,611 | * | 10/1996 | Ralph et al. | 435/69.51 |
| 5,650,150 | * | 7/1997 | Gillies | 424/134.1 |
| 5,705,478 | * | 1/1998 | Boime | 514/8 |

FOREIGN PATENT DOCUMENTS

| | | |
|---|---|---|
| WO9319777 | 10/1993 | (WO) . |
| WO 95/31544 | 11/1995 | (WO) . |

OTHER PUBLICATIONS

Narayan, Prema et al., "Functional expression of yoked human chorionic gonadotropin in baculovirus-infected insect cells.", Molecular Endocrinology, vol. 9, No. 12, pp. 1719–1726 (1995).
Johnson, Gregory A. et al., "Baculovirus-insect cell production of bioactive choriogonadotropin-immunoglobulin in G heavy-chain fusion proteins in sheep.", Biology of Reproduction, vol. 52, pp. 68–73 (1995).
Wu, Chengbin et al., "Protein engineering of a novel constitutively active hormone-receptor complex.", Journal of Biological Chemistry, vol. 271, No. 49, pp. 31638–31642 (1996).
Smith, Richard et al., "The active form of tumor necrosis factor is a trimer.", Journal of Biological Chemistry, col 262, No. 15, pp. 6951–6954 (1987).
Eck, Michael et al., "The structure of tumor necrosis factor-alpha at 2.6 A resolution.", Journal of Biological Chemistry, vol. 264, No. 29, pp. 17595–17605 (1989).
Jones, E. Y. et al., "Structure of tumor necrosis factor.", Nature, vol. 338, pp. 225–228 (1989).
Eck, Michael et al., "The structure of human lymphotoxin (tumor necrosis factor–beta) at 1.9 A resolution." Journal of Biological Chemistry, vol. 267, No. 4, pp. 2119–2122 (1992).
Pierce, John et al., "Glycoprotein hormones structure and function.", Department of Biological Chemistry, Univ. of Cal., (1991).
Lapthorn, A. J. et al., "Crystal structure of human chorionic gonadotropin.", Nature, vol. 369, pp. 455–461 (1994).
Wu, Hao et al., "Structure of human chorionic gonadotropin at 2.6–A resolution from MAD analysis of the selenomethionyl protein.", Structure, vol. 2, No. 6, pp. 545–558 (1994).
Englemann, Hartmut et al., "Antibodies to a soluble form of a tumor necrosis factor (TNF) receptor have TNF–like activity.", Journal of Biological Chemistry, vol. 265, No. 24, pp. 14497–14504 (1990).
Adam, Dieter et al., "Cross–linking of the p55 tumor necrosis factor receptor cytoplasmic domain by a dimeric ligand induces nuclear factor–κbeta and mediates cell death.", Journal of Biological Chemistry, vol. 270, No. 29, pp. 17482–17487 (1995).
Loetscher, Hansruedi et al., "Recombinant 55–kda tumor necrosis factor (tnf) receptor.", Journal of Biological Chemistry, col. 266, No. 27, pp. 18324–18329 (1991).
Banner, David W. et al., "Crystal structure of the soluble human 55kd tnf receptor–human tnfbeta complex: implications for tnf receptor activation.", Cell, vol. 73, pp. 431–445 (1993).
Pennica, Diane et al., "Biochemical characterization of the extracellular domain of the 75–kilodalton tumor necrosis factor receptor.", Biochemistry, vol. 32, pp. 3131–3138 (1993).
Engelmann, Hartmut et al., "Two tumor necrosis factor–binding proteins purified from human urine.", Journal of Biological Chemistry, vol. 265, No. 3, pp. 1531–1536 (1990).
Van Zee, Kimberly et al., "Tumor necrosis factor soluble receptors circulate during experimental and clinical inflammation and can protect against excessive tumor necrosis factor aolha in vitro and in vivo." Proc. Natl. Acad. Sci., col. 89, pp. 4845–4849 (1992).

(List continued on next page.)

*Primary Examiner*—Lorraine Spector
(74) *Attorney, Agent, or Firm*—Browdy and Neimark

(57) ABSTRACT

A hybrid protein includes two coexpressed amino acid sequences forming a dimer. Each sequence contains the binding portion of a receptor, such as TBP1 or TBP2, or a ligand, such as IL-6, IFN-β and TPO, linked to a subunit of a heterodimeric proteinaceous hormone, such as hCG. Each coexpressed sequence contains a corresponding hormone subunit so as to form a heterodimer upon expression. Corresponding DNA molecules, expression vectors and host cells are also disclosed as are pharmaceutical compositions and a method of producing such proteins.

15 Claims, 12 Drawing Sheets

OTHER PUBLICATIONS

Aderka, Dan et al., "Stabilization of th bioactivity of tumor necrosis factor by its soluble receptors.", J. Exp. Med., col. 175, pp. 323–329 (1992).

Mohler, Kendall et al., "Soluble tumor necrosis factor (tnf) receptors are effective therapeutic agents in lethal endotoxemia and function simultaneously as both tnf carriers and tnf antagonists.", Journal of Immunology, vol. 151, No. 3, pp. 1548–1561 (1993).

Bertini, Riccardo et al., "Urinary tnf–binding protein (tnf soluble receptor) protects mice against the lethal effect of tnf and endotoxic shock.", Eur. Cytokine Netw., vol. 4, No. 1, pp. 39–42 (1993).

Piguet, P. F. et al., "Evolution of collagen arthritis in mice is arrested by treatment with anti–tumor necrosis factor (tnf) antibody or a recombinant tnf receptor.", Immunology, vol. 77, pp. 510–514 (1992).

Williams, Richard et al., "Successful therapy of collagen–induced arthritis with tnf receptor–IgG fusion protein and combination with anti–CD4.", Immunology, vol. 84, pp. 433–439 (1995).

Capon, Daniel et al., "Designing CD4 immunoadhesions for AIDS therapy." Nature, vol. 337, pp. 525–531 (1989).

Ashkenzazi, Avi et al., "Protection against endotoxic shock by a tumor necrosis factor receptor immunoadhesion.", Proc. Natl. Acad. Sci. USA, vol. 88, pp. 10535–10539 (1991).

Suitters, Amanda et al., "Differential effect of isotype on efficacy of anti–tumor necrosis factor alpha chimeric antibodies in experimental septic shock.", J. Exp. Med., vol. 179, pp. 849–856 (1994).

Nolan, Oria et al., "Bifunctional antibodies: concept, production and applications.", Biochemica et Biophysica Acta, vol. 1040, pp. 1–11 (1990).

Rodriques, Maria L. et al., "Engineering Fab' fragments for efficient f9ab)$_2$ formation in *escherichia coli* and for improved in vivo stability.", Journal of Immunology, vol. 151, No. 12, pp. 6954–6961 (1993).

Chang, Hsiu–Ching et al., "A general method for facilitating heterodimeric pairing between two proteins: application to expression of alpha and beta t–cell receptor extracellular segments.", Proc. Natl. Acad. Sci. USA, vol. 91, pp. 11408–11412 (1994).

Kirk, Zining et al., "Solution assembly of a soluble, heteromeric, high affininty interleukin–2 receptor complex.", Journal of Biological Chemistry, vol. 270, No. 27, pp. 16039–16044 (1995).

Bazzioni, F. et al., "Chimeric tumor necrosis factor receptors with constitutive signaling activity.", Proc. Natl. Acad. Sci. USA, vol. 92, pp. 5376–5380 (1995).

Boldin, Mark et al., "Self–association of the "Death domains" of the p55 tumor necrosis factor (tnf) receptor and fas/apo1 prompts signaling for tnf and fas/apo1 effects.", Journal of Biological Chemistry, vol. 270, No. 1, pp. 387–391 (1995).

Vu, Thien Khai et al., "Molecular cloning of a functional thrombin receptor reveals a novel proteolytic mechanism of receptor activation.", Cell, vol. 64, 1057–1068 (1991).

Song, Ho Yeong et al., "Aggregation of the intracellular domain of the type I tumor necrosis factor receptor defined by the two–hybrid system.", J. of Biological Chemistry, vol. 269, No. 36, pp. 22492–22495 (1994).

Russell, Deborah et al., "Combined inhibition of interleukin–1 and tumor necrosis factor in rodent endotoxemia: improved survival and organ function.", J. Infectious Diseases, vol. 171, pp. 1528–38 (1995).

Rao, Ch. et al., "Stability of human chorionic gonadotropin and its alpha subunit in human blood.", Am. J. Obstet. Gynecol., vol. 146, No. 1, pp. 65–68 (1983).

Damewood, Marian et al., "Disappearance if exogenously administered human chorionic gonadotropin.", Fertility and Sterility, vol. 52, No. 3, pp. 398–400 (1989).

Chen, Fang et al., "The carboxy–terminal region of the glycoprotein hormone alpha–subunit: contributions to receptor binding and signaling in human chorionis gonadotropin.", Molecular Endocrinology, vol. 6. (1992).

Abstract of Bielinska, M. et al., "Site–directed mutagenesis identifies two receptor binding domains in the human chorionic gonadotropin alpha subunit.", Membrane Receptors, No. 1844.

Furuhashi, Madoka et al., "Fusing the carboxy–terminal peptide of the chronic gonadotropin (cg) beta–subunit to the common alpha–subunit: retention of o–linked glycosylation and enhanced in vivo bioactivity of chimeric human cg.", Molecular Endocrinology, vol. 9, No. 1, pp. 54–63 (1995).

Sugahra, Tadashi et al., "Biosynthesis of a biologically active single peptide chain containing the human common alpha and chorionic gonadotropin beta subunits in tandem.", Proc. Natl. Acad. Sci. USA, vol. 92, pp. 2041–2045 (1995).

Urlaub, Gail et al., "Isolation of chinese hamster cell mutants deficient in dihydrofolate reductase activity.", Proc. Natl. Acad. Sci. USA, vol. 77, No. 7, pp. 4216–4220 (1980).

Nophar, Yaron et al., "Soluble forms of tumor necrosis factor receptors (tnf–rs).", The EMBO Journal, vol. 9, No. 10, pp. 3269–3278 (1990).

Fiddes, John et al., "Isolation, cloning and sequence analysis of the cDNA for the alpha–subunit of human chorionic gonadotropin.", Nature, vol. 281, pp. 351–356 (1979).

Fiddes, John et al., "The cDNA for the beta–subunit of human chorionic gonadotropin suggests evolution of a gene by readthrough into the 3'–untranslated region.", Nature, vol. 286, (1980).

Campbell, Robert et al., "Conversion of human choriogonadotropin into a follitropin by protein engineering." Proc. Natl. Acad. Sci. USA, vol. 88, pp. 760–764 (1991).

Cole, Edward et al., "Recombinant human thyroid stimulating hormone: development of a biotechnology product for detection of metastatic lesions of thyroid cancer.", Biotechnology, vol. 11, pp. 1014–1024 (1993).

Gluzman, Yakov. "SV40–transformed simian cells support the replication of early SV40 mutants.", Cell, vol. 23, pp. 175–182 (1981).

Chu, Gilbert., "Electroporation for the efficient transfection of mammalian cells with DNA.", Nucleic Acids Research, vol. 15, No. 3 (1987).

Yen, Janie et al., "A rapid in vitro cytotoxicity assay for the detection of tumor necrosis factor on human BT–20 cells.", Journal of Immunotherapy, vol. 10, pp. 174–181 (1991).

* cited by examiner

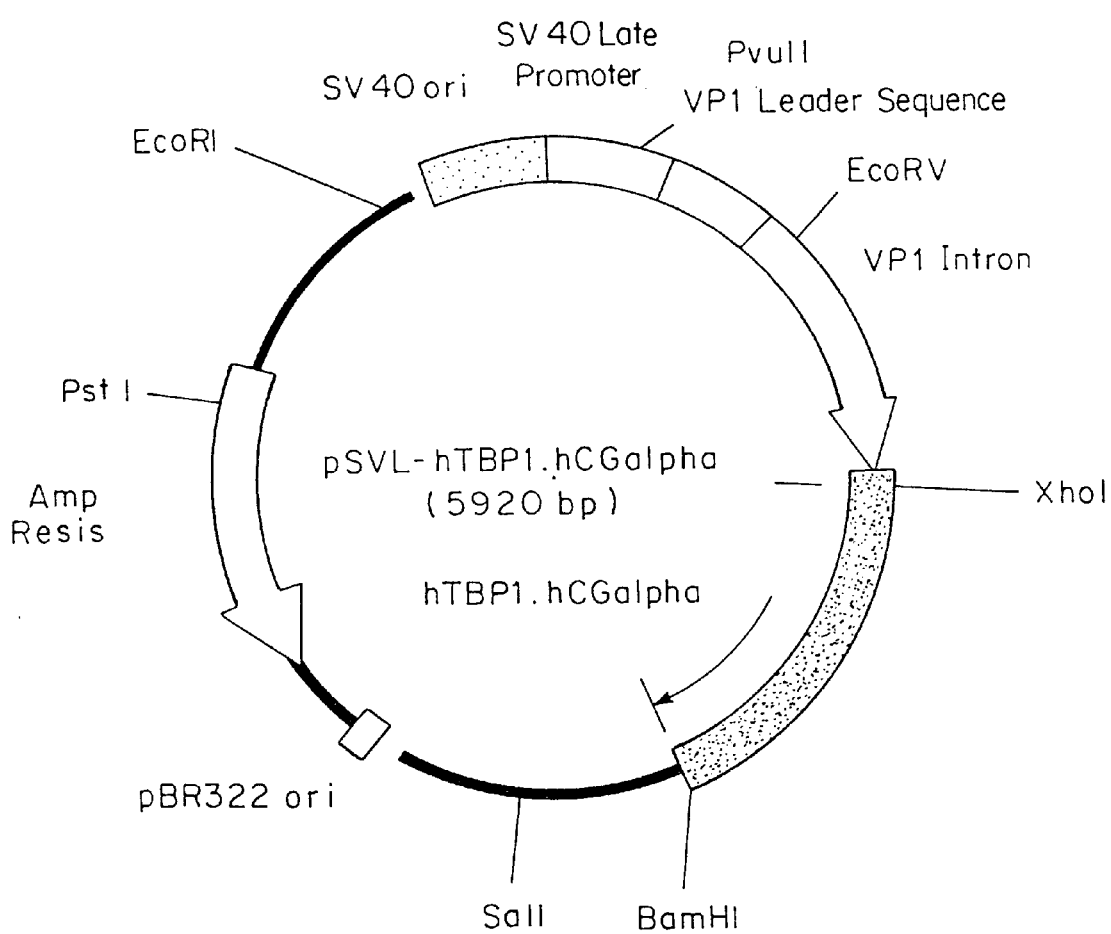
FIG. 1a(1)

FIG. 1a(2)

hGH Signal Sequence      hGH Intron

XhoI
TCGAG ATG GCT ACA G GTAAGCGCCCCTAAATCCCTTGGCACAATGTGTCCTGAGGGGAGAGCAGCCAGACCTGTAGATGGGACGGGGGCACTAACCCTCAGGTTTGGGGTTTCT
     Met Ala Thr

GAATGTGAGTATCGCCATGTAAGCCCAGTATTTGGCCAATCTCAGAAAGCTCCTGGTCCCTGGAGGATGGAGAGAGAAAAACAAACAGCTCCTGAGCAGGAGAGTGCTGGCCTCTTGCTTTC

CGGGCTCCCTCTGTTGCCCTCTGGTTTCTCCCCAGGC TCC CGG ACG TCC CTG CTC CTG GCT TTT GGC CTG CTG CTG TGC CTG CCC TGG CTT
    ▸Ser Arg Thr Ser Leu Leu Leu Ala Phe Gly Leu Leu Leu Cys Leu Pro Trp Leu
  +20 Asp of Processed TBP1

CAA GAG GGC AGT GCC GAT AGT GTG TGT CCC CAA GGA AAA TAT ATC CAC CAA AAT AAT TCG ATT TGC TGT ACC AAG TGC CAC AAA AAA
Gln Glu Gly Ser Ala Asp Ser Val Cys Pro Gln Gly Lys Tyr Ile His Pro Gln Asn Asn Ser Ile Cys Cys Thr Lys Cys His Lys Gly

ACC TAC TTG TAC AAT GAC TGT CCA GGC CCG GGG CAG CAG GAT ACG GAT CGG CAG TGT GAG GAG TCC TTC ACC GCT TCA GAA AAC CAC CTC
Thr Tyr Leu Tyr Asn Asp Cys Pro Gly Pro Gly Gln Gln Asp Thr Asp Arg Gln Cys Glu Glu Ser Phe Thr Ala Ser Glu Asn His Leu

AGA CAC TGC CTC AGC TGT TCC AAA TGC CGA AAG GAA ATG GGT GTG CAG TGT GAG ATC TCT TCT TGC GAC GTG GAC CGG ACC GTG TGT GGC TGC
Arg His Cys Leu Ser Cys Ser Lys Cys Arg Lys Glu Met Gly Val Gln Cys Glu Ile Ser Ser Cys Thr Val Asp Arg Thr Val Cys Gly Cys

AGG AAG AAC CAG TAC CGG CAT TAT TGG AGT GAA AAC CTT TTT CAG TGC CTC AAT GGG ACC GTG CAC CTC TCC TGT
Arg Lys Asn Gln Tyr Arg His Tyr Trp Ser Glu Asn Leu Phe Gln Cys Leu Asn Gly Thr Val His Leu Ser Cys
                                                                                                             Linker CAG GAG AAA CAG AAC ACC GTG TGC CAT GCA GGT TTC TTT CTA AGA GAA AAC GAG TGT TCC TGT *GCC GGT GCT GCC CCA GGT*
Gln Glu Lys Gln Asn Thr Val Cys His Ala Gly Phe Phe Leu Arg Glu Asn Glu Cys Ser Cys *Ala Gly Ala Ala Pro Gly*
+7 Cys of hCG alpha TGC CCA GAA TGC ACG CTA CAG CAG GAA AAC CCA TTC TTC TCC CAG CCG GGT GCC CCA ATA CTT CAG TGC ATG GGC TGC TGC TTC TCT AGA GCA TAT
Cys Pro Glu Cys Thr Leu Gln Gln Glu Asn Pro Phe Phe Ser Gln Pro Gly Ala Pro Ile Leu Gln Cys Met Gly Cys Cys Phe Ser Arg Ala Tyr CCC ACT CCA AGG TCC AAG AAG ACG ATG TTG GTC CAA AAG AAC GTC ACT TCA GAG TCC ACT TGC TGT GTA GCT AAA TCA TAT AAC AGG GTC
Pro Thr Pro Arg Ser Lys Lys Thr Met Leu Val Gln Lys Asn Val Thr Ser Glu Ser Thr Cys Cys Val Ala Lys Ser Tyr Asn Arg Val ACA GTA ATG GGG GGT TTC AAA GTG GAG AAC CAC ACG GCG TGC CAC TGC AGT ACT TGT TAT TAT CAC AAA TCT TAA G
Thr Val Met Gly Gly Phe Lys Val Glu Asn His Thr Ala Cys His Cys Ser Thr Cys Tyr Tyr His Lys Ser ...
                                                                                                                                                                                                  | BamIII

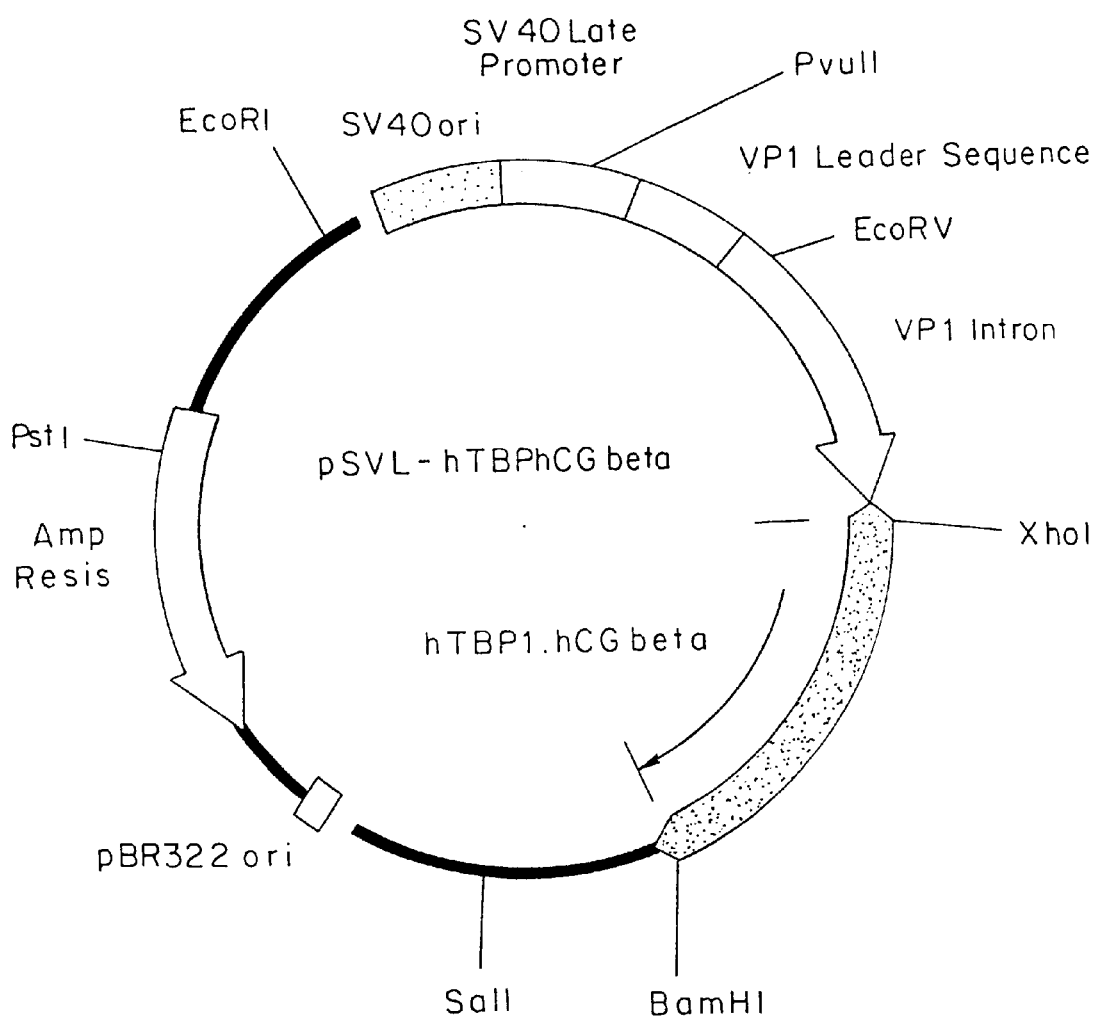
FIG. 1b(1)

FIG. 1b(2)

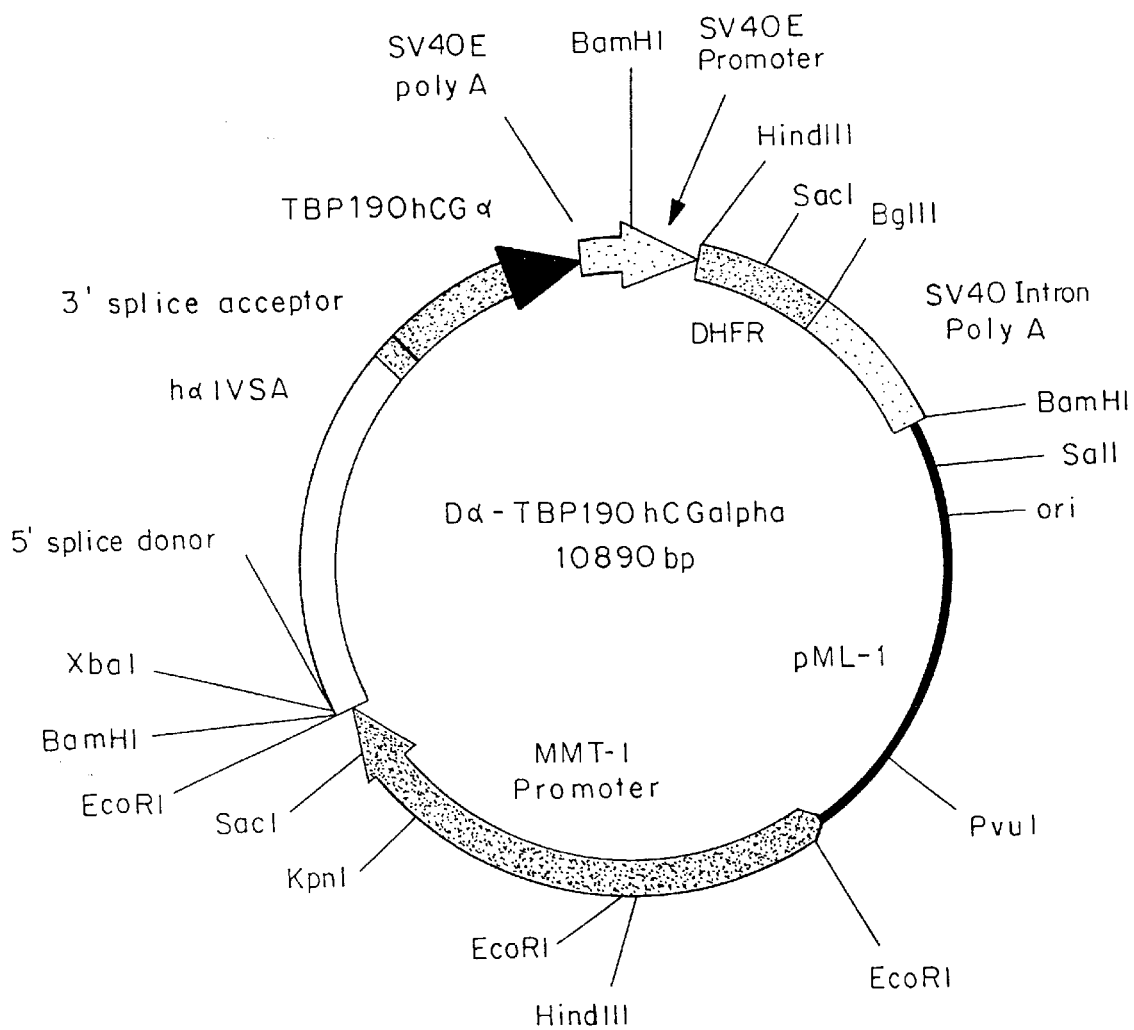
FIG. 2a(1)

FIG. 2a(2)

```
XhoI         hGH Signal Sequence                              hGH Intron
TCGAG ATG GCT ACA G GTAAGCGCCCCCTAAAATCCCTTTGGGCACAATGTGTCCTGAGGGGAGAGGCAGGACCTGTAGATGGAAGGGGGCACTAACCCTCAGGTTTGGGGTTTCT
      ▲Met Ala Thr GAATGTGAGTATCGCCATGTAAGCCCAGTATTTGGCCAATCTCAGAAAGCTCCTGGTCCCTGAGGGATGGAGAGAGAAAACAAACAGCTCCTGGAGCAGGAGAGTGCTGGCCTCTTGCTCTC CGGCTCCCTCTGTTGCCCTCTGGTTTCTCCCAGGC  TCC CGG ACG TCC CTG CTC CTG GCT TTT GGC CTG CTG CCC TGG CTT
                                     ▲Ser Arg Thr Ser Leu Leu Leu Ala Phe Gly Leu Leu Cys Leu Pro Trp Leu
                                     +20 Asp of processed TBP1

CAA GAG GGC AGT GCC GAT AGT GTG TGT CCC CAA GGA AAA TAT ATC CAC CCT CAA AAT TCG ATT TGT ACC AAG TGC CAC AAA GGA
Gln Glu Gly Ser Ala Asp Ser Val Cys Pro Gln Gly Lys Tyr Ile His Pro Gln Asn Ser Ile Cys Cys Thr Lys Cys His Lys Gly

ACC TAC TTG TAC AAT GAC TGT CCA GGC CCG GGG GAC CAG AAG GAG ATG ACG GAG TGT GAG AGG TGC TCA GAA AAC CAC CTC
Thr Tyr Leu Tyr Asn Asp Cys Pro Gly Pro Gly Asp Gln Lys Glu Met Thr Glu Cys Glu Arg Cys Ser Glu Asn His Leu

AGA CAC TGC AGC TGC CTC TCC AAA TGC TAT CGG CAT GCA GGT GAA AAC CTT TTC CAG TGC CTA CCC TGC ACC GTG TGC TCC TGC
Arg His Cys Ser Cys Leu Ser Lys Cys Tyr Arg His Ala Gly Glu Asn Leu Phe Gln Cys Leu Pro Cys Thr Val Cys Ser Cys

AGG AAG AAC CAG CAG TAC TGC CAT TAT AGT GGT GGA GAA ATG ACT GAG TGT GTC TCC GGG ACC GTG CAC CTC TCC TGC
Arg Lys Asn Gln Gln Tyr Cys His Tyr Ser Gly Gly Glu Met Thr Glu Cys Val Ser Gly Thr Val His Leu Ser Cys

CAG GAG AAA CAG AAC ACC GTG TGC CTA CCC CAG ATT GAG AAT GTT AAG GGC ACT GAG GAC TCA GGC ACC GCC GGT GCT GCC TGC CCA
Gln Glu Lys Gln Asn Thr Val Cys Leu Pro Gln Ile Glu Asn Val Lys Gly Thr Glu Asp Ser Gly Thr Ala Gly Ala Ala Pro Gly Cys Pro
                                                                                    Linker        +7 Cys of hCG alpha GAA TGC ACG AAG TTG TGC TAC TTC TCC CAG GAA AAC CCA TTC TTC TCC CAG CCG GGT GCC CCA ATA CTT CAG TGC ATG GGC TGC TGC TTC AGA GCA TAT CCC ACT
Glu Cys Thr Lys Leu Cys Tyr Phe Ser Gln Glu Asn Pro Phe Phe Ser Gln Pro Gly Ala Pro Ile Leu Gln Cys Met Gly Cys Cys Phe Ser Arg Ala Tyr Pro Thr CCA CTA AGG TCC AAG AAG ACG ATG TTG GTC AAG AAC CAC ACC TCA GAG TCC TGC TGT GTA GCT AAA TCA GCT ACA AGG GTC ACA GTA
Pro Leu Arg Ser Lys Lys Thr Met Leu Val Gln Lys Asn Val Thr Ser Glu Ser Cys Cys Val Ala Lys Ser Tyr Asn Arg Val Thr Val ATG GGG GGT TTC AAA GTG GAG AAC CAC ACG GCG TGC CAC TGC AGT ACT TGT TAT TAT CAC AAA TCT TAA GGATCCCTCGAG
Met Gly Gly Phe Lys Val Glu Asn His Thr Ala Cys His Cys Ser Thr Cys Tyr Tyr His Lys Ser ***
                                                                               Bam HI  XhoI
```

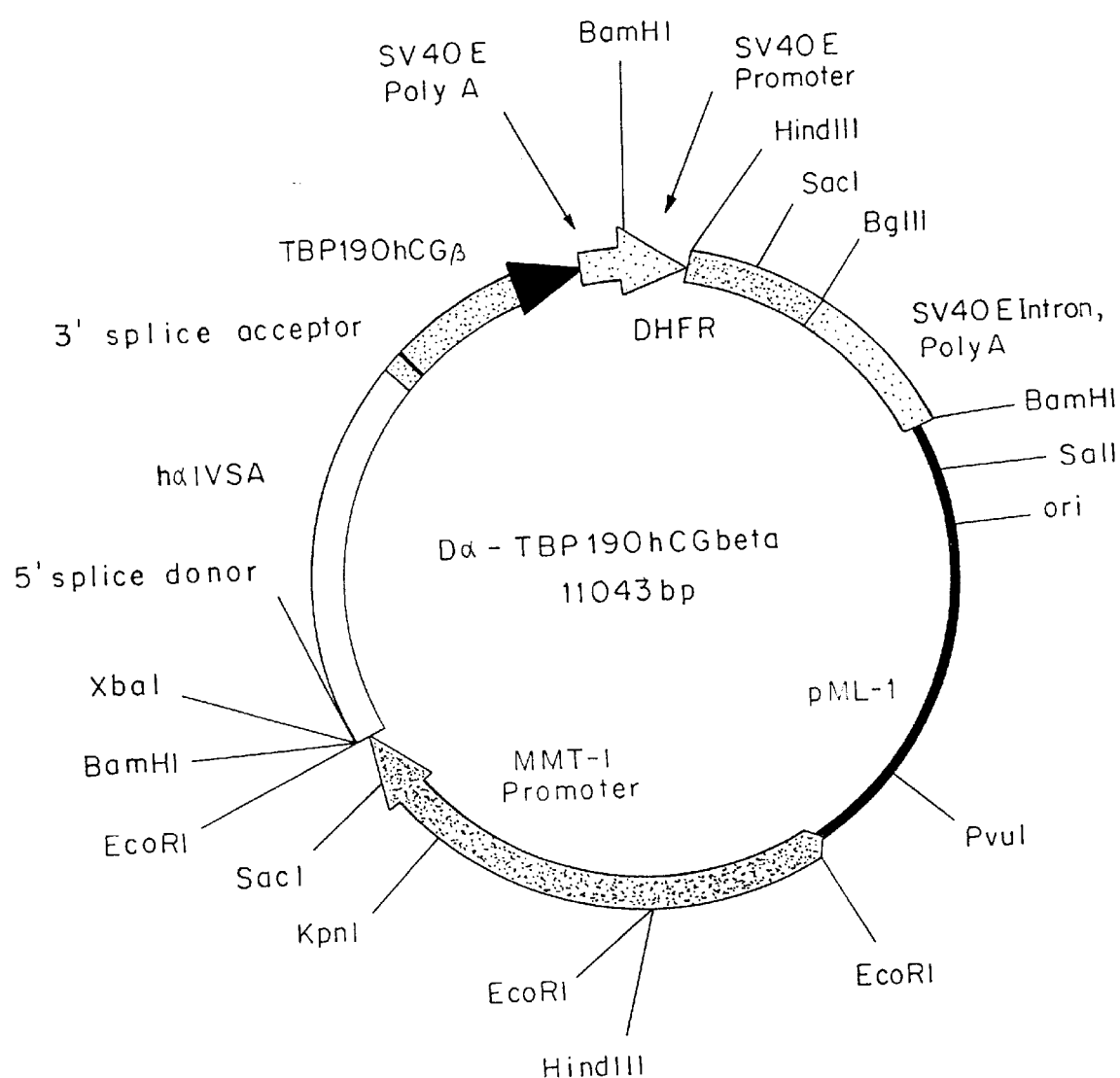
FIG. 2b(1)

FIG. 2b(2)

```
XhoI          hGH Signal Sequence                    hGH Intron
CTCGAG ATG GCT ACA G GTAAGCGCCCCTAAATCCCTTTGGGCACAATGTGTCCTGAGGGGAGAAGCAGCGACCTGTAGATGGGACGGGGGCACTAACCCTCAGGTTTGGG
       ▶Met Ala Thr
GGTTCTGAATGTGAGTGTGGCCATGTAAGCCCATGTTGCCCTCTGTTCTCCCCCAGGAAAAGTCCTGATATTGGCCAATCTCAGAAAGTCCTGTCCTGAGGGATGGAGAGAGAAAAACAAACAGCTCCTGTAGCAGTGAGTGCTGC CTCTTGCTCTCCGGCTCCCCTCTGTTGCCCTCTGGTTTCTCCCCAGG C TCC CGG ACG TCC CTG CTC CTG GCT TTT GGC CTG CTC TGC CTG
                                                 ▶Ser Arg Thr Ser Leu Leu Leu Ala Phe Gly Leu Leu Cys Leu
                                                 +20 Asp of Processed TBP1
CCC TGG CTT CAA GAG GGC AGT GCC   GAT AGT GTG TGT CCC CAA GGA AAA TAT ATC CAC CCT CAA AAT AAT TCG ATT TGC TGT ACC
▶Pro Trp Leu Gln Glu Gly Ser Ala  Asp Ser Val Cys Pro Gln Gly Lys Tyr Ile His Pro Gln Asn Asn Ser Ile Cys Cys Thr AAG TGC CAC AAA GGA ACC TAC TTG TAC AAT GAC TGT CCA GGG CCG CAG GAT ACG GAC TGC AGG GAG TGT GAG AGC GGC TCC TTC ACC
▶Lys Cys His Lys Gly Thr Tyr Leu Tyr Asn Asp Cys Pro Gly Pro Gln Asp Thr Asp Cys Arg Glu Cys Glu Ser Gly Ser Phe Thr GCT TCA GAA AAC CAC CTC AGA CAC TGC CTC AGC TGC CGA AAG TGC CGA AAG GAA ATG GGT CAG GTG GAG ATC TCT TCT TGC ACA GTG GAC
▶Ala Ser Glu Asn His Leu Arg His Cys Leu Ser Cys Arg Lys Cys Arg Lys Glu Met Gly Gln Val Glu Ile Ser Ser Cys Thr Val Asp CGG GAC ACC GTG TGT GGC TGT AAG AAG AAC CAG TAC CGG CAT TAT TGG AGT GAA AAC CTT TTC CAG TGC TTC AAT TGC AGC CTC TGC CTC
▶Arg Asp Thr Val Cys Gly Cys Lys Lys Asn Gln Tyr Arg His Tyr Trp Ser Glu Asn Leu Phe Gln Cys Phe Asn Cys Ser Leu Cys Leu AAT GGG ACC GTG CAC CTC TCC TGC CAG GAG AAA CAG AAC ACC GTG TGC CAT GCA GGT TTC CTA AGA GAA AAC GAG TGT GTC
▶Asn Gly Thr Val His Leu Ser Cys Gln Glu Lys Gln Asn Thr Val Cys His Ala Gly Phe Leu Arg Glu Asn Glu Cys Val TCC TGT AGT AAC TGT AAG AAA AGC CTG GAG TGC ACG AAG CTG TGC CTA CCC CAG ATT GAG AAT GTT AAG GGC AAT GAC TCA GGC ACC
▶Ser Cys Ser Asn Cys Lys Lys Ser Leu Glu Cys Thr Lys Leu Cys Leu Pro Gln Ile Glu Asn Val Lys Gly Thr Asp Ser Gly Thr
   Linker    +7 Pro of beta
ACA GCT GGT GCT GGT CCA CGG TGC CGC CCC ATC AAT GCC CGG TGC CGT GTG GAG AAG GAG TGC CCC GTG TGC ATC ACC GTC AAC
▶Thr Ala Gly Ala Gly Pro Arg Cys Arg Pro Ile Asn Ala Thr Leu Ala Val Glu Lys Glu Cys Pro Val Cys Ile Thr Val Asn ACC ACC ATC TGT GCC GGC TAC TGC CCC ACC ATG TGC CGC GTG CTG CAG GGG GTC CTG CCG GCC CTG CCC CAG CTG GTG TGC AAC TAC CGC
▶Thr Thr Ile Cys Ala Gly Tyr Cys Pro Thr Met Cys Arg Val Leu Gln Gly Val Leu Pro Ala Leu Pro Gln Leu Val Cys Asn Tyr Arg GAT GTG CGC TTC GAG TCC ATC CGG CTC CCT GGC TGC CCC CGG CTG GTC TCC TAC GCC GTG GCT CTC AGC TGT CAA TGT
▶Asp Val Arg Phe Glu Ser Ile Arg Leu Pro Gly Cys Pro Arg Leu Val Ser Tyr Ala Val Ala Leu Ser Cys Gln Cys GCA CTC TGC CGC CGC AGC ACC GAC TGC GGT GGG CCC AAG GAC GAC CAC CCC TTG ACC TGT GAT GAC CCC CGC CGC TTC CAG GAC TCC TCT TCC
▶Ala Leu Cys Arg Arg Ser Thr Asp Cys Gly Gly Pro Lys Asp Asp His Pro Leu Thr Cys Asp Asp Pro Arg Arg Phe Gln Asp Ser Ser Ser TCA AAG GCC CCT CCC CCC AGC CTT CCA AGC CCA CTC CGA CTC CCG CCC TCG GAC ACC CCG ATC CTC CCA CAA TAA   GGATCCCTCGAG
▶Ser Lys Ala Pro Pro Pro Ser Leu Pro Ser Pro Leu Pro Ser Arg Leu Pro Pro Ser Asp Thr Pro Ile Leu Pro Gln ***   BamHI XhoI
``` p55 TNFR1, TBP1 and TBP1 FUSION CONSTRUCTS

HYBRID HETERODIMERIC PROTEIN HORMONE

CROSS REFERENCE TO RELATED APPLICATION

This application claims the benefit of U.S. Provisional Application No. 60/011,936, filed Feb. 20, 1996.

FIELD OF THE INVENTION

The present invention relates to a hybrid protein comprising two coexpressed amino acid sequences forming a dimer, each comprising:

a) at least one amino acid sequence selected from a homomeric receptor, a chain of a heteromeric receptor, a ligand, and fragments thereof; and b) a subunit of a heterodimeric proteinaceous hormone or fragments thereof; in which (a) and (b) are bonded directly or through a peptide linker, and, in each couple, the two subunits (b) are different and capable of aggregating to form a dimer complex.

BACKGROUND OF THE INVENTION

Protein-protein interactions are essential to the normal physiological functions of cells and multicellular organisms. Many proteins in nature exhibit novel or optimal functions when complexed with one or more other protein chains. This is illustrated by various ligand-receptor combinations that contribute to regulation of cellular activity. Certain ligands, such as tumor necrosis factor α (TNFα), TNFβ, or human chorionic gonadotropin (hCG), occur as multi-subunit complexes. Some of these complexes contain multiple copies of the same subunit. TNFα and TNFβ (collectively referred to hereafter as TNF) are homotrimers formed by three identical subunits (1–4). Other ligands are composed of non-identical subunits. For example, hCG is a heterodimer (5–7). Receptors may also occur or function as multi-chain complexes. For example, receptors for TNF transduce a signal after being aggregated to form dimers (8,9). Ligands to these receptors promote aggregation of two or three receptor chains, thereby affording a mechanism of receptor activation. For example, TNF-mediated aggregation activates TNF receptors (10–12).

The modulation of protein-protein interactions can be a useful mechanism for therapeutic intervention in various diseases and pathologies. Soluble binding proteins, that can interact with ligands, can potentially sequester the ligand away from the receptor, thereby reducing the activation of that particular receptor pathway. Alternatively, sequestration of the ligand may delay its elimination or degradation, thereby increasing its duration of effect, and perhaps its apparent activity in vivo. In the case of TNF, soluble TNF receptors have been primarily associated with inhibition of TNF activity (13–17).

Soluble binding proteins may be useful for treating human diseases. For example, soluble TNF receptors have been shown to have efficacy in animal models of arthritis (18,19).

Since TNF has three binding sites for its receptor (10–12), and dimerization of the cell surface receptor is sufficient for bioactivity (8,9), it is likely that binding of a single soluble receptor to TNF will leave open the possibility that this 1:3 complex of soluble receptor:TNF (trimer) can still bind and activate a pair of cell surface TNF receptors. To achieve an inhibitory effect, it would be expected that two of the receptor binding sites on the TNF trimer must be occupied or blocked by the soluble binding protein. Alternatively, the binding protein could block proper orientation of TNF at the cell surface.

Generally speaking, the need was felt of synthesizing proteins that contain two receptor (or ligands) chains, as dimeric hybrid protein. See Wallach et al., U.S. Pat. No. 5,478,925.

The primary strategy employed for generating dimeric or multimeric hybrid proteins, containing binding domains from extracellular receptors, has been to fuse these proteins to the constant regions of an antibody heavy chain.

This strategy led, for example, to the construction of CD4 immunoadhesins (20). These are hybrid molecules consisting of the first two (or all four) immunoglobulin-like domains of CD4 fused to the constant region of antibody heavy and light chains. This strategy for creating hybrid molecules was adapted to the receptors for TNF (10,16,21) and led to the generation of constructs with higher in vitro activity than the monomeric soluble binding proteins.

It is widely held that the higher in vitro potency of the dimeric fusion proteins should translate into higher in vivo activity. One study does support this, revealing an at least 50-fold higher activity for a p75(TBP2)-Ig fusion protein in protecting mice from the consequences of intravenous LPS injection (16).

However, despite the widespread utilization of immunoglobulin fusion proteins, this strategy has several drawbacks. One is that certain immunoglobulin Fc domains participate in effector functions of the immune system. These functions may be undesirable in a particular therapeutic setting (22).

A second limitation pertains to the special cases where it is desirable to produce heteromeric fusion proteins, for example soluble analogs of the heteromeric IL-6 or type I interferon receptors. Although there are numerous methods for producing bifunctional antibodies (e.g., by co-transfection or hybridoma fusions), the efficiency of synthesis is greatly compromised by the mixture of homodimers and heterodimers that typically results (23). Recently there have been several reports describing the use of leucine zipper motifs to guide assembly of heterodimers (24–26). This appears to be a promising approach for research purposes, but the non-native or intracellular sequences employed may not be suitable for chronic applications in the clinic due to antigenicity. The efficiency of assembly and stability post assembly may also be limitations.

On the other hand, in the particular case of TNF receptors, certain modifications to the p55 TNF receptor have been found to facilitate homodimerization and signaling in the absence of ligand (27,28). It has been found that a cytoplasmic region of the receptor, termed the "death domain," can act as a homodimerization motif (28,30). As an alternative to an immunoglobulin hybrid protein, fusion of the extracellular domain of the TNF receptor to its cytoplasmic death domain could conceivably result in a secreted protein which can dimerize in the absence of TNF. Such fusion proteins have been disclosed and claimed in the International Patent Application WO 95/31544.

A third further strategy employed for generating dimers of soluble TNF receptors has been to chemically cross-link the monomeric proteins with polyethylene glycol (31).

SUMMARY OF THE INVENTION

An alternative for obtaining such dimeric proteins, offering some important advantages, is the one of the present invention and consists in using a natural heterodimeric scaffold corresponding to a circulating non-immunoglobulin protein with a long half-life. A preferred example is hCG, a protein that is secreted well, has good stability, and has a long half-life (32–33). Given hCG's prominent role as a marker of pregnancy, many reagents have been developed to quantitate and study the protein in vitro and in vivo. In addition, hCG has been extensively studied using mutagenesis, and it is known that small deletions to the protein, such as removal of five residues at the extreme carboxyl-terminus of the α subunit, can effectively eliminate its biological activity while preserving its capability to form heterodimer (34,35). Small insertions, of up to 30 amino acids, have been shown to be tolerated at the amino- and carboxyl-termini of the α subunit (36), while fusion of the α subunit to the carboxyl terminus of the β subunit also had little effect on heterodimer formation (37).

An analog of hCG in which an immunoglobulin Fc domain was fused to the C-terminus of hCG β subunit has also been reported; however, this construct was not secreted and no effort was made to combine it with an α subunit (38).

Therefore, the main object of the present invention is a hybrid protein comprising two coexpressed amino acid sequences forming a dimer, each comprising:

a) at least one amino acid sequence selected among a homomeric receptor, a chain of a heteromeric receptor, a ligand, and fragments thereof; and b) a subunit of a heterodimeric proteinaceous hormone, or fragments thereof; in which (a) and (b) are bonded directly or through a peptide linker, and in each couple the two subunits (b) are different and capable of aggregating forming a dimer complex.

According to the present invention, the linker may be enzymatically cleavable.

Sequence (a) is preferably selected among: the extracellular domain of the TNF Receptor 1 (55 kDa, also called TBP1), the extracellular domain of the TNF Receptor 2 (75 kDa, also called TBP2), or fragments thereof still containing the ligand binding domain; the extracellular domains of the IL-6 receptors (also called gp80 and gp130); the extracellular domain of the IFN α/β receptor or IFN γ receptor; a gonadotropin receptor or its extracellular fragments; antibody light chains, or fragments thereof, optionally associated with the respective heavy chains; antibody heavy chains, or fragments thereof, optionally associated with the respective light chains; antibody Fab domains; or ligand proteins, such as cytokines, growth factors or hormones other than gonadotropins, specific examples of which include IL-6, IFN-β, TPO, or fragments thereof.

Sequence (b) is preferably selected among a hCG, FSH, LH, TSH, inhibin subunit, or fragments thereof.

Modifications to the proteins, such as chemical or protease cleavage of the protein backbone, or chemical or enzymatic modification of certain amino acid side chains, can be used to render the components of the hybrid protein of the invention inactive. This restriction of activity may also be accomplished through the use of recombinant DNA techniques to alter the coding sequence for the hybrid protein in a way that results directly in the restriction of activity to one component, or that renders the protein more amenable to subsequent chemical or enzymatic modification.

The above hybrid proteins will result in monofunctional, bifunctional or multifunctional molecules, depending on the amino acid sequences (a) that are combined with (b). In each couple, (a) can be linked to the amino termini or to the carboxy termini of (b), or to both.

A monoclonal hybrid protein of the present invention can, for instance, comprise the extracellular domain of a gonadotropin receptor linked to one of the corresponding receptor-binding gonadotropin subunits. According to such an embodiment, the hybrid protein of the invention can be a molecule in which, for example, the FSH receptor extracellular domain is linked to FSH to increase plasma half-life and improve biological activity.

This preparation can be employed to induce follicular maturation in assisted reproduction methods, such as ovulation induction or in vitro fertilization, and to serve as a means to dramatically amplify the biological activity of the hormone essential for the success of the process, thus reducing the requirement for both the hormone itself and the number of injections to achieve ovulation.

The FSH receptor and the production of the extracellular domain of the human FSH receptor have been described respectively in WO 92/16620 and WO 96/38575.

According to a particular embodiment, the extracellular domain of the FSH receptor (ECD) can be fused in frame with a peptide linker that contains the thrombin recognition/cleavage site (29) and represents a "tethered" arm. The peptide linker links the extracellular domain of FSH with a FSH subunit. This will allow for removal of the extracellular domain of the FSH receptor by cleavage at the thrombin cleavage site as the molecule comes in contact with thrombin in the systemic circulation.

In another embodiment, instead of the thrombin cleavage site, an enzyme recognition site for an enzyme that is found in greatest abundance in the ovary is used. In this way, as the ECD-FSH molecule travels to the ovary, it will be exposed to enzymes found in the highest concentrations in that tissue and the ECD will be removed so that the FSH can interact with the membrane bound receptor.

In yet another embodiment, instead of an enzyme recognition site, a flexible hinge region is cloned between ECD and FSH so that the ECD will not be enzymatically removed from the hormone. In this way, when the ECD-FSH molecule arrives at the ovary, a competition will be established between the hinge-attached ECD and the ECD of the FSH receptor found on the ovarian cell membrane.

In a further preferred embodiment of the invention, the hybrid protein consists of the aggregation between a couple of aa sequences, one of which contains TBP1 (or the fragments from aa 20 to aa 161 or to aa 190) as (a) and the α subunit of hCG as (b), and the other contains always TBP1 (or the same fragments as above) as (a) and the β subunit of hCG, or fragments thereof, as (b). According to this embodiment, depending on the particular sequence that is chosen as (b) (the entire β subunit of hCG, or fragments or modifications thereof), the resulting hybrid protein will have one activity (only that of TBP1) or a combination of activities (that of TBP1 with that of hCG). In this latter case the hybrid protein can be used, for example, in the combined treatment of Kaposi's sarcoma and metabolic wasting in AIDS.

In a further embodiment of the invention, one or more covalent bonds between the two subunits (b) are added to enhance the stability of the resulting hybrid protein. This can be done, e.g., by adding one or more non-native interchain disulfide bonds. The sites for these cross-links can be deduced from the known structures of the heterodimeric hormones. For example, a suitable site in hCG could be to place cysteine residues at α subunit residue Lys45 and β subunit residue Glu21, replacing a salt bridge (non-covalent bond) with a disulfide bond (covalent bond). Another object of the present invention are PEGylated or other chemically modified forms of the hybrid proteins.

A further object of the present invention is a DNA molecule comprising the DNA sequence coding for the above hybrid protein, as well as nucleotide sequences substantially the same. "Nucleotide sequences substantially the same" includes all other nucleic acid sequences which, by virtue of the degeneracy of the genetic code, also code for the given amino acid sequence.

For the production of the hybrid protein of the invention, the DNA sequence (a) is obtained from existing clones, as is (b). The DNA sequence coding for the desired sequence (a) is ligated with the DNA sequence coding for the desired sequence (b). Two of these fused products are inserted and ligated into a suitable plasmid or each into a different plasmid. Once formed, the expression vector, or the two expression vectors, is introduced into a suitable host cell, which then expresses the vector(s) to yield the hybrid protein of the invention as defined above.

The preferred method for preparing the hybrid of the invention is by way of PCR technology using oligonucleotides specific for the desired sequences to be copied from the clones encoding sequences (a) and (b).

Expression of any of the recombinant proteins of the invention as mentioned herein can be effected in eukaryotic cells (e.g., yeasts, insect or mammalian cells) or prokaryotic cells, using the appropriate expression vectors. Any method known in the art can be employed.

For example the DNA molecules coding for the proteins obtained by any of the above methods are inserted into appropriately constructed expression vectors by techniques well known in the art (see Sambrook et al, 1989). Double stranded cDNA is linked to plasmid vectors by homopolymeric tailing or by restriction linking involving the use of synthetic DNA linkers or blunt-ended ligation techniques: DNA ligases are used to ligate the DNA molecules and undesirable joining is avoided by treatment with alkaline phosphatase.

In order to be capable of expressing the desired protein, an expression vector should comprise also specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the hybrid protein of the invention is inserted into a vector(s), having the operably linked transcriptional and translational regulatory signals, which is capable of integrating the desired gene sequences into the host cell. The cells which have been stably transformed by the introduced DNA can be selected by also introducing one or more markers which allow for selection of host cells which contain the expression vector. The marker may also provide for phototrophy to a auxotropic host, biocide resistance, e.g., antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g., mammalian cells, such as human, monkey, mouse, and Chinese hamster ovary (CHO) cells, because they provide post-translational modifications to protein molecules, including correct folding or glycosylation at correct sites. Also, yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence(s) results in the production of the desired proteins.

Purification of the recombinant proteins is carried out by any one of the methods known for this purpose, i.e., any conventional procedure involving extraction, precipitation, chromatography, electrophoresis, or the like. A further purification procedure that may be used in preference for purifying the protein of the invention is affinity chromatography using monoclonal antibodies which bind the target protein and which are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

The term "hybrid protein", as used herein, generically refers to a protein which contains two or more different proteins or fragments thereof.

As used herein, "fusion protein" refers to a hybrid protein, which consists of two or more proteins, or fragments thereof, linked together covalently.

The term "aggregation", as used herein, means the formation of strong specific non-covalent interactions between two polypeptide chains forming a complex, such as those existing between the α and β subunit of a heterodimeric hormone (such as FSH, LH, hCG or TSH).

The terms "ligand" or "ligand protein", as used herein, refer to a molecule, other than an antibody or an immunoglobulin, capable of being bound by the ligand-binding domain of a receptor; such molecule may occur in nature, or may be chemically modified or chemically synthesised.

The term "ligand-binding domain", as used herein, refers to a portion of the receptor that is involved in binding a ligand and is generally a portion or essentially all of the extracellular domain.

The term "receptor", as used herein, refers to a membrane protein, whose binding with the respective ligand triggers secondary cellular responses that result in the activation or inhibition of intracellular process.

In a further aspect, the present invention provides the use of the hybrid protein as a medicament. The medicament is preferably presented in the form of a pharmaceutical composition comprising the protein of the invention together with one or more pharmaceutically acceptable carriers and/or excipients. Such pharmaceutical compositions represent yet a further aspect of the invention.

BRIEF DESCRIPTION OF THE DRAWINGS

The invention will be better understood by reference to the appended drawings, in which:

FIGS. 1(a) and 1(b) show the TBP(20-161)-hCGα and TBP(20-161)-hCGβ constructs, respectively, and the corresponding sequences (SEQ ID NOS:1–4).

FIGS. 2(a) and 2(b) show the TBP(20-190)-hCGα and TBP(20-190)-hCGβ constructs, respectively, and the corresponding sequences (SEQ ID NOS:5–8).

DETAILED DESCRIPTION OF THE PREFERRED EMBODIMENTS

Figure 3:
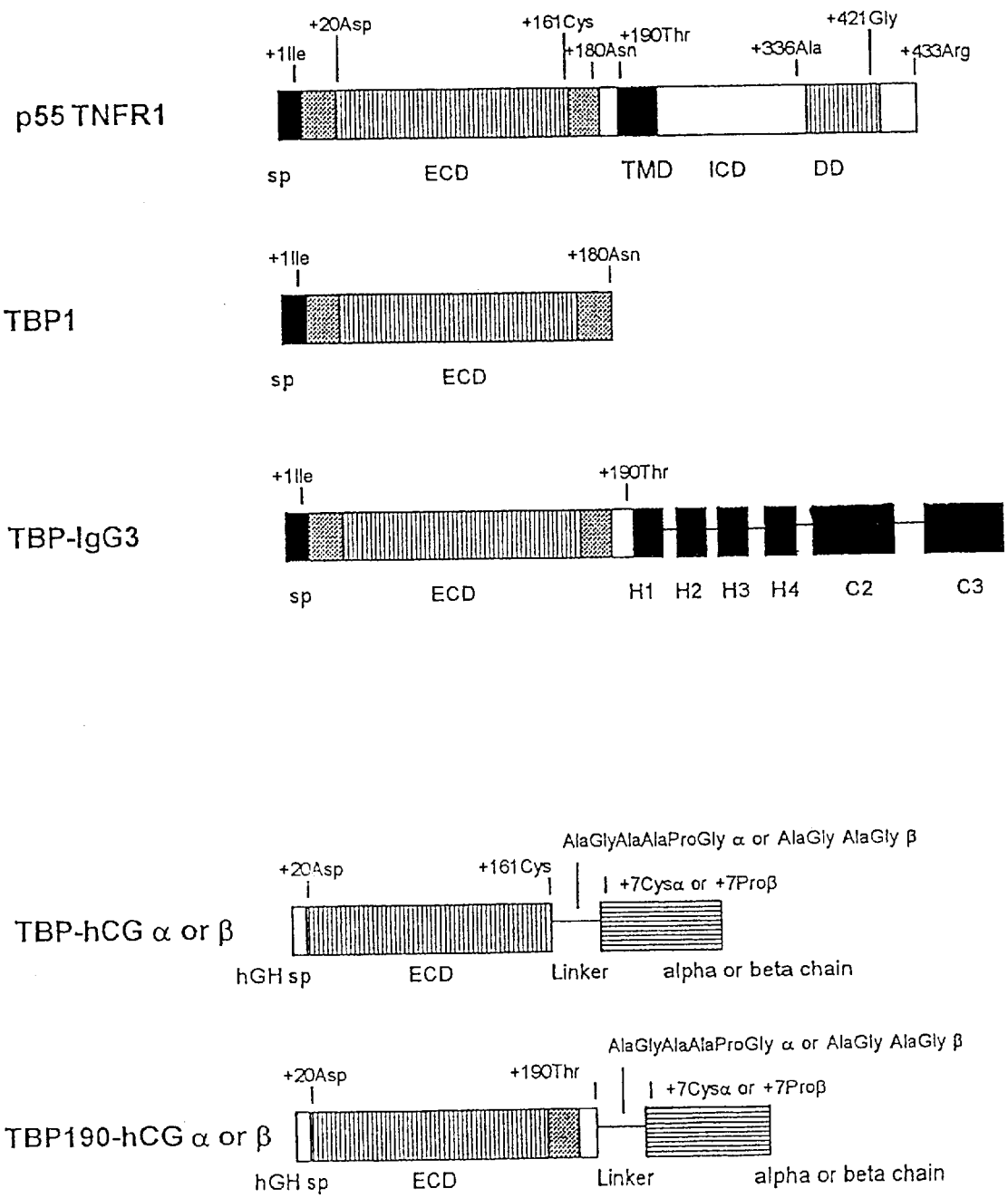
FIG. 3 is a schematic summary of the constructs of FIGS. 1 and 2 showing p55 TNFR1, TBP1 and TBP1 fusion contructs. The linker sequences shown on the last two lines are SEQ ID NO:9 (Ala-Gly-Ala-Ala-Pro-Gly) and SEQ ID NO:10 (Ala-Gly-Ala-Gly).

The invention will now be described by means of the following Examples, which should not be construed as in any way limiting the present invention.

EXAMPLES

Materials and Methods

Cell lines used in this study were obtained from the American Type Culture Collection (ATCC), 10801 University Boulevard, Manassas, Va. 20110-2209, unless otherwise specified. The CHO-DUKX cell line was obtained from L. Chasin at Columbia University through D. Houseman at MIT (39). The CHO-DUKX cells, which lack a functional gene for dihydrofolate reductase, were routinely maintained in complete α-plus Modified Eagles Medium (α(+)MEM) supplemented with 10% fetal bovine serum (FBS). The COS-7 cells were routinely maintained in Dulbecco's Modified Eagles Medium (DMEM) supplemented with 10% FBS. Unless specified otherwise, cells were split to maintain them in log phase of growth, and culture reagents were obtained from GIBCO (Grand Island, N.Y.).

1. Assembly of the genetic constructs encoding the hybrid proteins

The numbering assignments for the p55 TNF receptor are based on the cloning paper from Wallach (40), while the numbering assignments for the hCG subunits are based on the numbering assignments from the Fiddes cloning papers (41,42). The designation TBP, or TNF binding protein, refers to the extracellular domain portions of the TNF receptors capable of binding TNF. In these Examples, the DNA constructs will be named as TBP-hybrid proteins, with the partner and region of TBP indicated in the construct nomenclature. All of the TBP-hCG constructs contain the human growth hormone (hGH) signal peptide in place of the native p55 signal sequence. In addition, the hGH signal peptide has been placed so that it immediately precedes TBP residue Asp20, which is anticipated to make this the first residue in the mature, secreted protein. These modifications are not essential to the basic concept of using hCG as a partner of the hybrid protein.

The DNAs encoding the hybrid proteins were constructed using PCR methodology (43).

a. TBP1(20-161)-hCG

The initial TBP-hCG construct was engineered to contain the ligand binding domain from the extracellular region of the p55 TNF receptor (from Asp20 inclusive of residue Cys161) fused though a short linker to the hCG α and β subunits (starting at residues αCys7 or βPro7, respectively). This construct, hereafter referred to as TBP1(20-161)-hCG, is a heterodimer of two modified hCG subunits, TBP1(20-161)-hCGα and TBP1(20-161)-hCGβ.

The oligodeoxynucleotide primers used for the TBP1(20-161)-hCGα construct were:

```
primer 1(αβ)    TTT TCT CGA GAT GGC TAC AGG TAA GCG      (SEQ ID NO:11)
                CCC primer 2(α)     ACC TGG GGC AGC ACC GGC ACA GGA GAC ACA  (SEQ ID NO:12)
                CTC GTT TTC primer 3(α)     TGT GCC GGT GCT GCC CCA GGT TGC CCA GAA  (SEQ ID NO:13)
                TGC ACG CTA CAG primer 4(α)     TTT TGG ATC CTT AAG ATT TGT GAT AAT AAC  (SEQ ID NO:14)
                AAG TAC
```

These and all of the other primers described in these Examples were synthesized on an Applied Biosystems Model 392 DNA synthesis machine (ABI, Foster City, Calif.), using phosphoramidite chemistry.

Since both of the TBP-hCG subunit constructs have the same 5'-end (i.e., the 5'-end of the hGH/TBP construct), primer 1(αβ) was used for both TBP-hCG subunit constructs. The other primers used for the TBP1(20-161)-hCGβ construct were:

```
primer  CCG TGG ACC AGC ACC AGC ACA GGA GAC    (SEQ ID
2 (β)   ACA CTC GTT TTC                         NO:15)

primer  TGT GCT GGT GCT GGT CCA CGG TGC CGC    (SEQ ID
3 (β)   CCC ATC AAT                             NO:16)

primer  TTT TGG ATC CTT ATT GTG GGA GGA TCG    (SEQ ID
4 (β)   GGG TG                                  NO:17)
```

Primers 2(α) and 3(α) are reverse complements, and cover both the 3'-end of the coding region for the p55 extracellular domain, and the 5'-end of the hCG α subunit. Similarly, primers 2(β) and 3(β) are also reverse complements, and cover both the 3'-end of the coding region for the p55 extracellular domain, and the 5'-end of the hCG β subunit.

Two PCR reactions were run for each of the two TBP-hCG subunit constructs. The first used primers 1(αβ) and 2(α or β), and used as the template a plasmid encoding soluble p55 residues 20–180 preceded by the hGH signal peptide (plasmid pCMVhGHspcDNA.pA4). The second used primers 3(α or β) and 4(α or β), and used as the template either plasmid pSVL-hCGα or pSVL-hCGβ (44). The PCR was performed using Vent (TM) polymerase from New England Biolabs (Beverly, Mass.) in accordance with the manufacturer's recommendations, using for each reaction 25 cycles and the following conditions:

100 μg of template DNA

1 μg of each primer 2U of Vent(TM) polymerase (New England Biolabs)

denaturation at 99° C. for 30 seconds annealing at:

59° C. for 30 seconds for primers 1(αβ) and 2(α)

59° C. for 30 seconds for primers 3(α) and 4(α)

57° C. for 30 seconds for primers 1(αβ) and 2(β)

63° C. for 30 seconds for primers 3(β) and 4(β) extension at 75° C. for 75 seconds.

The PCR products were confirmed to be the expected size by electrophoresis in a 2% agarose gel and ethidium bromide staining. The fragments were then purified by passage over a Wizard column (Promega) in accordance with the column manufacturer's recommendations.

The final coding sequence for TBP1(20-161)-hCGα was assembled by fusion PCR using primer 1(αβ) and primer 4(α), and using as template the purified products from the p55 and hCG α fragments obtained from the first PCR reactions. First the two templates, which due to the overlap between primers 2(α) and 3(α) could be denatured and annealed together, were passed through 10 cycles of PCR in the absence of any added primers. The conditions for these cycles were essentially the same as those used earlier, except that the annealing was done at 67° C. and the extension was performed for 2 minutes. At the end of these 10 cycles, primers 1(αβ) and 4(α) were added, and another 10 cycles were performed. The conditions for this final set of reactions was the same as used earlier, except that an annealing temperature of 59° C. was used, and the extension was performed for 75 seconds.

Analysis of the products of this reaction by electrophoresis in a 1% agarose gel confirmed that the expected fragment of about 1100 bp was obtained. The reaction was passed over a Wizard column to purify the fragment, which was then digested with XbaI and BamHI and re-purified in a 0.7% low-melting point agarose gel. The purified fragment was subcloned into plasmid PSVL (Pharmacia), which had first been digested with XbaI and BamHI and gel purified on a 0.8% low-melting point agarose gel. Following ligation with T4 ligase, the mixture was used to transform AG1 E. coli and then plated onto LB/ampicillin plates for overnight culture at 37° C. Plasmid DNAs from ampicillin-resistant colonies were analyzed by digestion with XhoI and BamHI to confirm the presence of the insert (which is excised in this digest). Six clones were found to contain inserts, and one (clone 7) was selected for further advancement and designated pSVLTBPhCGα (containing TBP1(20-161)-hCGα). Dideoxy DNA sequencing (using Sequenase™, U.S. Biochemicals, Cleveland, Ohio) of the insert in this vector confirmed that the construct was correct, and that no undesired changes had been introduced.

The final coding sequence for TBP1(20-161)-hCGβ was assembled in a manner similar to that described for TBP1 (20-161)-hCGα using fusion PCR and primers 1(αβ) and 4(β), and using as template the purified products from the p55 and hCG β fragments obtained from the first PCR reactions. The resulting PSVL plasmid containing the insert of interest was designated pSVLTBPhCGβ.

b. TBP(20-190)-hCG

A second set of TBP-hCG proteins was prepared by modification of the TBP(20-161)-hCG constructs to produce an analog containing TBP spanning from Asp20 to Thr190, in place of the 20-161 region in the initial analog. This was done by replacing the fragment between the BglII and XbaI sites in plasmid pSVLTBPhCGα with a PCR fragment containing the change. This PCR fragment was generated using fusion PCR. The primers were:

| | | |
|---|---|---|
| primer 1 | TTT TAG ATC TCT TCT TGC ACA GTG GAC | (SEQ ID NO:18) |
| primer 2 | TGT GGT GCC TGA GTC CTC AGT | (SEQ ID NO:19) |
| primer 3 | ACT GAG GAC TCA GGC ACC ACA GCC GGT GCT GCC CCA GGT TG | (SEQ ID NO:20) |
| primer 4 | TTT TTC TAG AGA AGC AGC AGC AGC CCA TG | (SEQ ID NO:21) |

Primers 1 and 2 were used to generate the sequence coding the additional p55 residues from 161–190. The PCR reaction was performed essentially as described earlier, using 1 μg of each primer and pUC-p55 as template. Similarly, primers 3 and 4 were used to generate by PCR the linker between the 3'-end of the TBP-coding region, and the 5'-end of the hCG α subunit coding region, using as a template plasmid pSVLTBPhCGα. Products from these PCR reactions were confirmed to be the correct size (about 296 bp and 121 bp respectively) by polyacrylamide gel electrophoresis (PAGE) on an 8% gel, and were then purified using a Wizard column. The design of primers 2 and 3 was such that they contained a region of overlap, so that the two PCR products (from primers 1 and 2, and from primers 3 and 4) could be annealed for fusion PCR with primers 1 and 4. Subsequent to the fusion reaction, the desired product of about 400 bp was confirmed and purified using a 1.5% agarose gel and a Wizard column. This DNA was then digested with BglII and XbaI, and ligated with BglII/XbaI-digested pSVLTBPhCGα. The presence of an insert in plasmids isolated from transformed AG1 E. coli was confirmed by digestion with BglII and XbaI. The new construct was designated pSVLTBP(20-190)-hCGα.

Similarly, plasmid pSVLTBPhCGβ was modified by substitution of the BglII-XcmI fragment. However, this was done by subcloning of a single PCR product, rather than with a fusion PCR product. Primers 1 and 2b (see below) were used with pUC-p55 as the template.

```
primer 2b TTT TCC ACA GCC AGG GTG GCA TTG ATG GGG    (SEQ ID NO:22)

CGG CAC CGT GGA CCA GCA CCA GCT GTG GTG

CCT GAG TCC TCA GTG
```

The resulting PCR product (about 337 bp) was confirmed and purified as described above, digested with BglII and XcmI, and then ligated into BglII/XbaI-digested pSVLTB-PhCGβ. The presence of an insert in plasmids isolated from transformed AG1 E. coli was confirmed by digestion with BglII and XcmI. The new construct was designated pSVLTBP(20-190)-hCGβ.

The new constructs were subsequently confirmed by DNA sequencing.

In addition to producing these new pSVL-based plasmids, these constructs were also subcloned into other expression vectors likely to be more suitable for stable expression in CHO, particularly vector Dα, previously described as plasmid CLH3AXSV2DHFR (45). This was accomplished by converting a BamHI site flanking the inserts in the pSVL-based vectors to an XhoI site, and then excising the insert with XhoI and cloning it into XhoI digested Dα.

2. Transient and stable expression of the hybrid proteins

Transfections of COS-7 cells (ATCC CRL 1651, ref. 46) for transient expression of the TBP-hCG hybrid proteins were performed using electroporation (47). Exponentially growing COS-7 cells were removed by trypsinization, collected by gentle centrifugation (800 rpm, 4 minutes), washed with cold phosphate buffered saline (PBS), pH 7.3–7.4, and then repelleted by centrifugation. Cells were resuspended at a concentration of $5 \times 10^6$ cells per 400 μl cold PBS and mixed with 10 μg of plasmid DNA in a prechilled 2 mm gap electroporation cuvette. For cotransfections, 5 μg of each plasmid were used. The cuvette and cells were chilled on ice for a further 10 minutes, and then subjected to electroporation using a BTX Model 600 instrument and conditions of 125 V, 950 μF and R=8. Afterward the cells were set to cool on ice for 10 minutes, transferred to a 15 ml conical tube containing 9.5 ml complete medium (Dulbecco's modified Eagle's medium (DMEM) supplemented with 10% fetal bovine serum (FBS) and 1% L-glutamine) at room temperature, and left at room temperature for 5 minutes. After gentle mixing in the 15 ml tube, the entire contents was seeded onto two P100 plates and placed into a 37° C., 5% $CO_2$ incubator. After 18 hours the media was changed, and in some cases the new media contained only 1% or 0% FBS. After another 72 hours, the conditioned media was harvested, centrifuged to remove cells, and then stored frozen at −70° C.

Transfections of CHO-DUKX (CHO) cells for transient or stable expression were performed using calcium phosphate precipitation of DNA. Twenty-four hours prior to the transfection, exponentially growing CHO cells were plated onto 100 mm culture plates at a density of $7.5 \times 10^5$ cells per plate. On the day of the transfection, 10 μg of plasmid DNA was brought to 0.5 ml in transfection buffer (see below), 31 μl of 2 M $CaCl_2$ were added, the DNA-$CaCl_2$ solution was mixed by vortexing, and left to stand at room temperature for 45 minutes. After this the media was aspirated from the plates, the DNA was added to the cells using a sterile plastic pipette, and the cells were left at room temperature for 20 minutes. At the end of this period, 5 ml of complete α(+)MEM containing 10% FBS was added to the plates, which were incubated at 37° C. for 4–6 hours. The media was then aspirated off the plates, and the cells were subjected to a glycerol shock by incubating them with a solution of 15% glycerol in transfection buffer at 37° C. for 3.5 minutes. After removal of the glycerol solution, the cells were washed twice with PBS, refed with 10 ml complete α(+)MEM, 10% FBS, and returned to the 37° C. incubator. For stable transfections, after 48 hours the cells were split 1:10 and fed with selection medium (complete α-minus MEM (lacking nucleosides), 10% dialyzed FBS, and 0.02 μM methotrexate). Non-transfected (non-resistant) cells were typically eliminated in 3–4 weeks, leaving a population of transfected, methotrexate-resistant cells.

3. Quantitation of expression

Secretion of the hybrid proteins by transfected cells was assessed using a commercial assay kit for soluble p55 (R&D Systems; Minneapolis, Minn.) in accordance with the manufacturer's instructions. This assay also provides an estimate of the hybrid protein levels in conditioned and processed media, which served as the basis for selecting doses to be used in the bioassay.

4. Assessment of heterodimer formation

To assess the ability of the TBP-hCG subunit fusions to combine and form heterodimers, a sandwich immunoassay using antibodies to the hCG subunits was performed. In this assay, a monoclonal antibody to the hCG β subunit is coated onto microtiter plates and used for analyte capture. The primary detection antibody is a goat polyclonal raised against the human TSH α subunit (#082422G—Biodesign International; Kennenbunkport, Me.), which is in turn detected using a horse radish peroxidase conjugated rabbit anti-goat polyclonal antibody (Cappel; Durham, N.C.).

Several different anti-hCG β subunit antibodies were used in this work, all of which show no detectable cross-reactivity with the free α subunit. One of these antibodies (3/6) is used in the commercially available MAIAclone hCG assay kit (Biodata; Rome, Italy).

High-protein binding microtiter plates (Costar #3590) were coated with capture antibody by incubation (2 hours at 37° C.) with 100 μl/well of a 5 μg/ml solution of antibody in coating buffer (PBS, pH 7.4, 0.1 mM $Ca^{++}$, 0.1 mM $Mg^{++}$). After washing once with wash solution (PBS, pH 7.4+0.1% Tween 20) the plate is blocked by completely filling the wells (≈400 μl/well) with blocking solution (3% bovine serum albumin (BSA; fraction V—A-4503 Sigma) in PBS, pH 7.4) and incubating for one hour at 37° C. or overnight at 4° C. The plate is then washed twice with wash solution, and the reference and experimental samples, diluted in diluent (5 mg/ml BSA in PBS, pH 7.4) to yield a 100 µl volume, are added. After incubating the samples and the plate for two hours at 37° C., the plate is again twice washed with wash solution. The primary detection antibody, diluted 1:5000 in diluent, is added (100 µl/well) and incubated for one hour at 37° C. The secondary detection antibody (HRP conjugated rabbit anti-goat Ig), diluted 1:5000 in diluent, is added (100 µl/well) and after incubation for one hour at 37° C., the plate is washed three times with wash solution. One hundred µl of TMB substrate solution (Kirkegaard and Perry Laboratories) is added, the plate is incubated 20 minutes in the dark at room temperature, and then the enzymatic reaction is stopped by addition of 50 µl/well 0.3M $H_2SO_4$. The plate is then analyzed using a microtiter plate reader set for a wavelength of 450 nm.

5. Partial purification

To better quantitate the activities of these hybrid proteins, TBP-hCG hybrid proteins were partially purified by immunoaffinity chromatography. The antibody used was a monoclonal commercially available from R&D Systems (MAB #225). The column was CNBr-activated sepharose, charged with the antibody by following the manufacturer's (Pharmacia) instructions.

Conditioned media was collected from confluent T-175 flasks of each line using daily harvests of 50 ml SFMII media (GIBCO), five harvests for each line. The collections were subjected to centrifugation (1000 RPM) to remove cellular debris. The material was then assayed for TBP content using the commercial immunoassay and concentrated (Centricon units by Amicon; Beverly, Mass.) so that the apparent TBP concentration was about 50 ng/ml.

Ten ml of the concentrated TBP-hCG (sample #18873) was brought to approximately 1 M NaCl by addition of NaCl and adjustment of the solution to a conductivity of approximately 85 mS/cm. This was passed through a 0.5 ml anti-TBP immunoaffinity column. The flow-through was collected and run through the column a second time. After this the column was washed with 1 M NaCl in PBS. The bound TBP(20-161)-hCG was collected after elution with 50 mM citric acid (pH 2.5). The eluate (approximately 7 ml) was concentrated by filtration using Amicon Centricon-10's in accordance with the manufacturer's (Amicon) instructions, to a volume of approximately 200 µl. Approximately 800 µl of PBS was added to bring the sample volume to 1 ml, which was stored at 4° C. until tested by bioassay.

6. Assessment of anti-TNF activity

Numerous in vitro TNF-induced cytotoxicity assays have been described for evaluating analogs of soluble TNF receptors. We utilized an assay employing a human breast carcinoma cell line, BT-20 cells (ATCC HTB 19). The use of these cells as the basis for a TNF bioassay has been described previously (48). These cells are cultured at 37° C. in RPMI 1640 media supplemented with 10% heat-inactivated FBS. The cells were grown to a maximum 80–90% confluence, which entailed splitting every 3–4 days with a seeding density of about $3 \times 10^6$ cells per T175 $cm^2$ flask.

The BT-20 assay uses the inclusion of a cellular stain, crystal violet, as a detection method to assess survival of cells after treatment with TNF. Dead cells are unable to take up and retain the dye.

In brief, the protocol used for the assay of anti-TNF activity is the following. Recombinant human TNFα (R&D Systems) and the experimental samples are constituted in media (RPMI 1640 with 5% heat-inactivated FBS) and added to the wells of 96-well culture plates. The cells are then plated into these wells at a density of $1 \times 10^5$ cells/well. The quantity of TNFα added was determined earlier in titration studies, and represents a dose at which about 50% of the cells are killed.

After addition of the samples, the cells are cultured for 48 hours at 39° C., after which the proportion of live cells is determined using crystal violet staining and a microtiter plate reader (570 nm).

Results

1. Constructs under study

The designs of the hybrid proteins studied are briefly summarized below; two control proteins, a monomeric soluble p55 (r-hTBP-1) and a dimeric TBP-immunoglobulin fusion protein (TBP-IgG3) (prepared essentially as described in (10)), were studied for comparative purposes.

| Construct | TBP N-term | TBP C-term | Fusion partner |
|---|---|---|---|
| r-hTBP-1 | mix of 9 and 20 | 180 | none |
| TBP-IgG3 | mix of 9 and 20 | 190 | IgG3 heavy chain constant region |
| TBP (20-161)-hCG | 20 | 161 | hCGα and hCGβ (heterodimer) |
| TBP (20-190)-hCG | 20 | 190 | hCGα and hCGβ (heterodimer) |

Figure 1B:
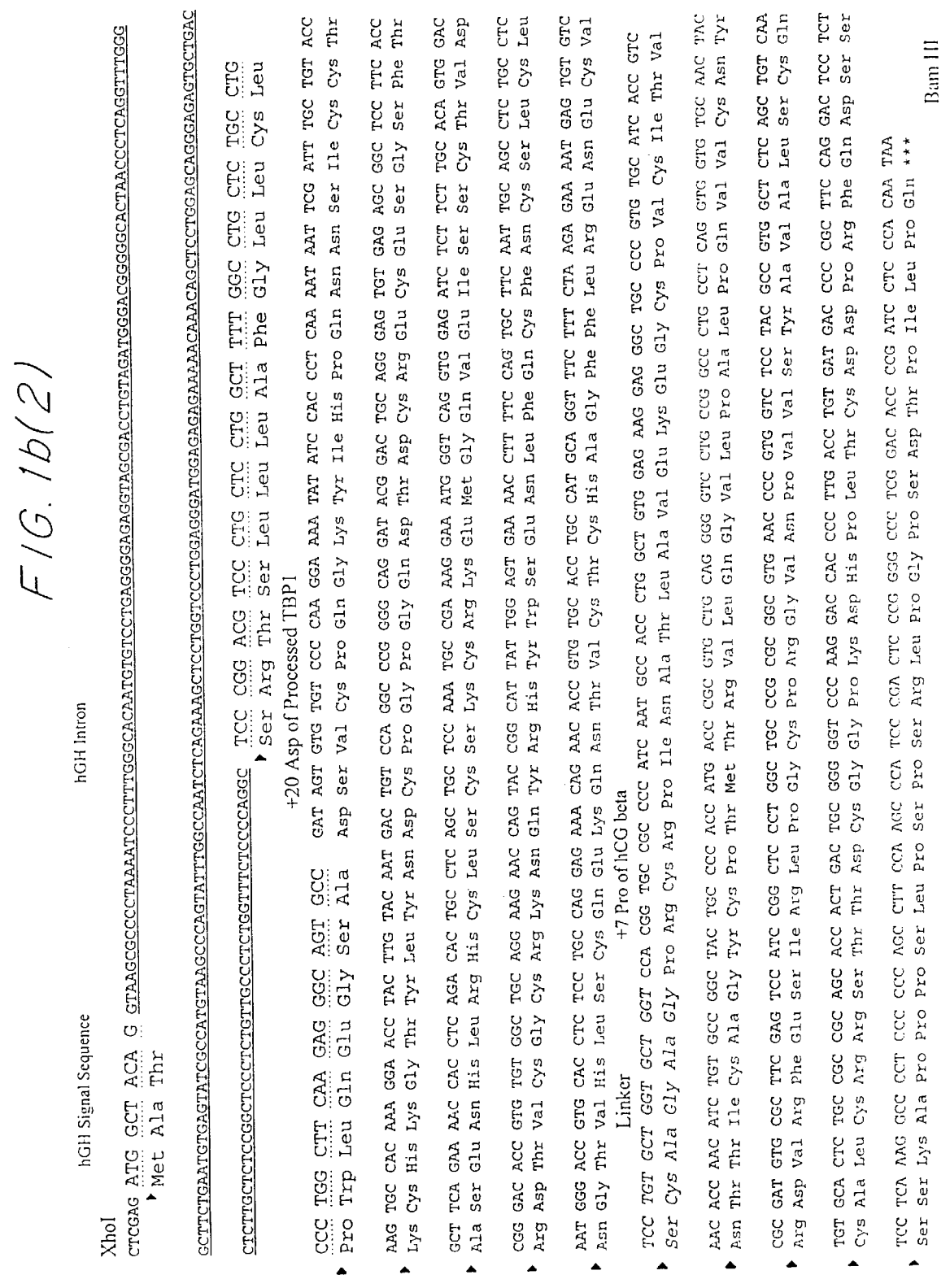

The sequences of the DNAs encoding, TBP(20-190)-hCG and TBP(20-161)-hCG are provided in FIGS. 1 and 2, respectively. A schematic summary of the constructs is provided in FIG. 3.

2. Secretion of TBP-hCG proteins

All of the constructs tested were found to be produced and secreted into culture media by transfected mammalian cells. Data illustrating this are shown in Tables 1 and 2.

TABLE 1

| COS-7 transient expression (TBP ELISA) | |
|---|---|
| Hybrid Protein | Concentration (pg/ml) |
| TBP1 | 66 |
| TBP-hCGα(20-161) | 5.1 |
| TBP-hCGβ(20-161) | 0.5 |
| TBP-hCG(20-161) | 2.7 |
| control | <0.25 |

TABLE 2

| COS-7 transient expression (TBP ELISA) | |
|---|---|
| Hybrid protein | Concentration (ng/ml) |
| TBP1 | 131 |
| TBP-hCGα(20-190) | 81 |
| TBP-hCGβ(20-190) | 9 |
| TBP-hCG(20-190) | 62 |
| control | <1 |

3. TBP-hCG(α/β) fusion proteins assemble into heterodimers

The combination of TBP-hCGα and TBP-hCGβ was confirmed using the sandwich assay for the hCG heterodimer. Only the combined transfection of α and β subunit fusions

TABLE 3

COS-7 transient expression
(hCG heterodimer assay)

| Hybrid Protein | Concentration (ng/ml) |
|---|---|
| TBP1 | <0.2 |
| TBP-hCGα(20-190) | <0.2 |
| TBP-hCGβ(20-190) | <0.2 |
| TBP-hCG(20-190) | 38 |
| control | <0.2 |

4. TBP-hCG hybrid proteins exhibit increased activity over TBP monomer

Hybrid proteins produced in either COS-7 or CHO cells were found to be potent inhibitors of TNFα in the BT-20 bioassay. Some of the samples tested are summarized in Table 4.

TABLE 4

Samples tested for anti-TNF activity

| Construct | Cell source | Nature of sample |
|---|---|---|
| r-hTBP-1 | CHO | purified |
| TBP-IgG3 | CHO | 1x conditioned media |
| TBP(20-161)-hCG | CHO | immunopurified (anti-TBP) |
| TBP(20-190)-hCG | CHO | 1x conditioned media |
| TBP(20-190)-hCG | COS | 1x conditioned media |

Negative controls (conditioned media from mock transfections) were included for the 1x media samples.

Figure 4:
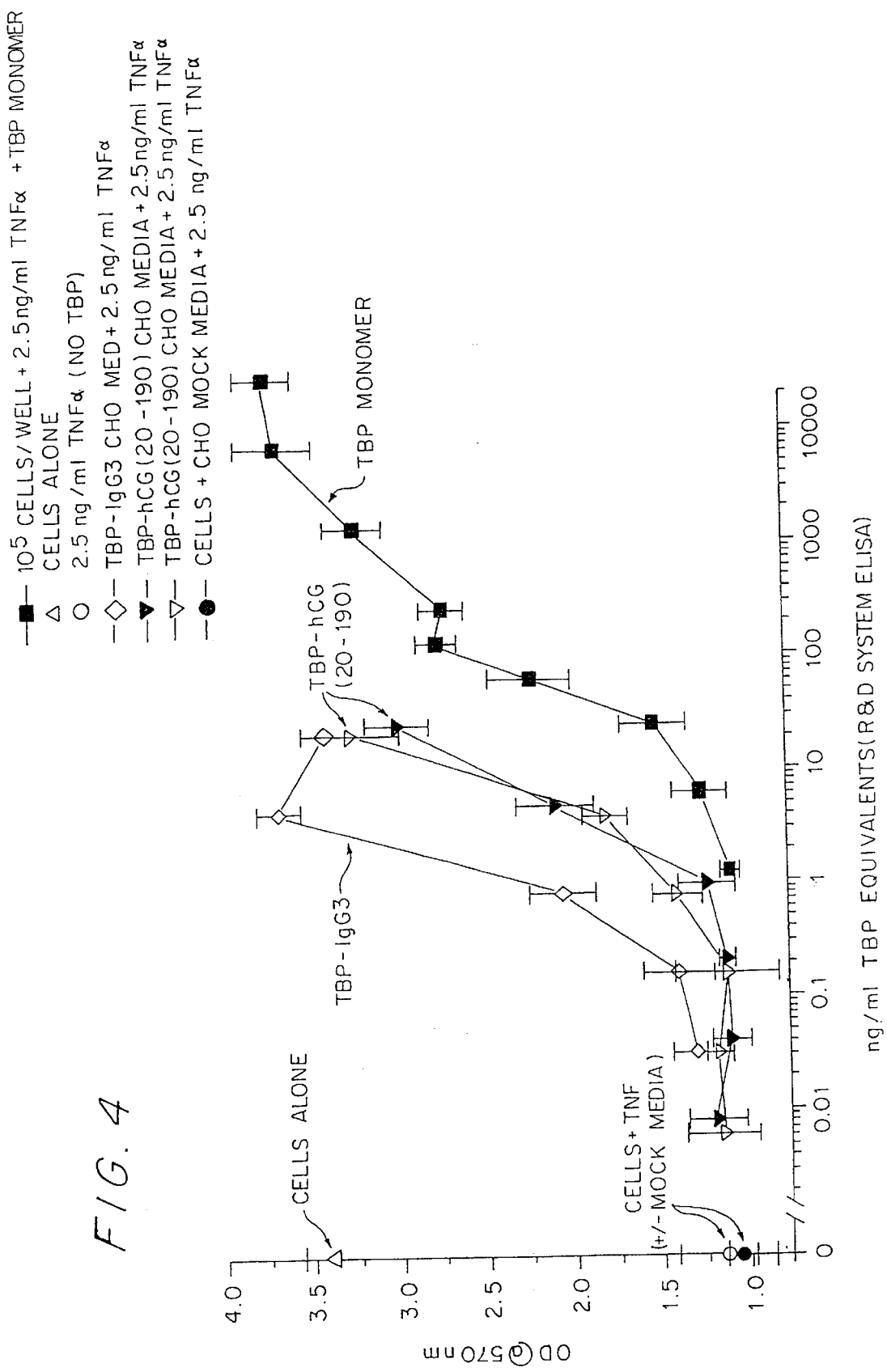
FIG. 4 is a graph illustrating the dose dependent protective effect of CHO cell expressed TBP-hCG(20-190) on TNFα-induced cytotoxicity on BT-20 cells and various controls.
Figure 5:
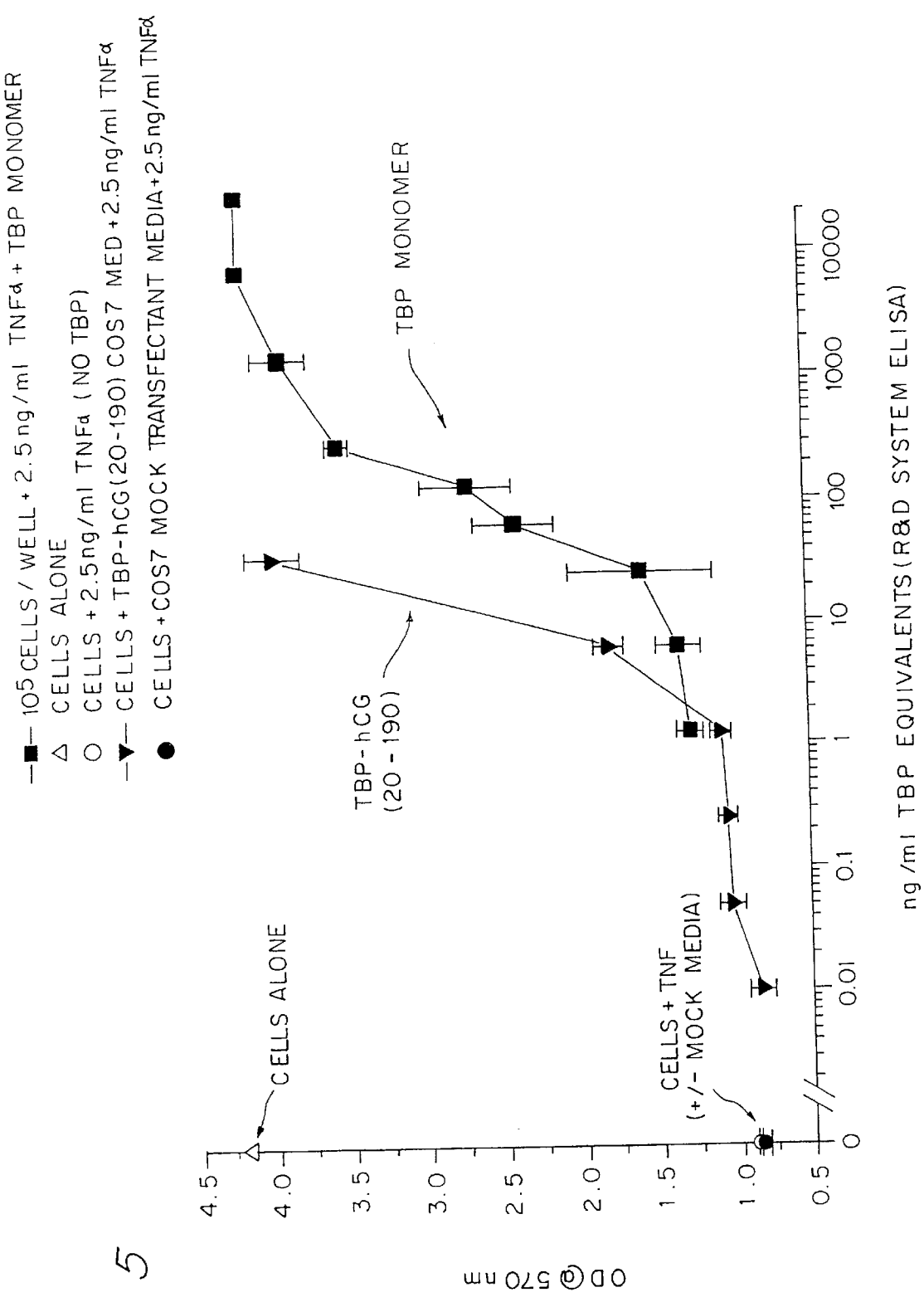
FIG. 5 is a graph illustrating the dose dependent protective effect of COS cell expressed TBP-hCG(20-190) on TNFα-induced cytotoxicity on BT-20 cells and various controls.
Figure 6:
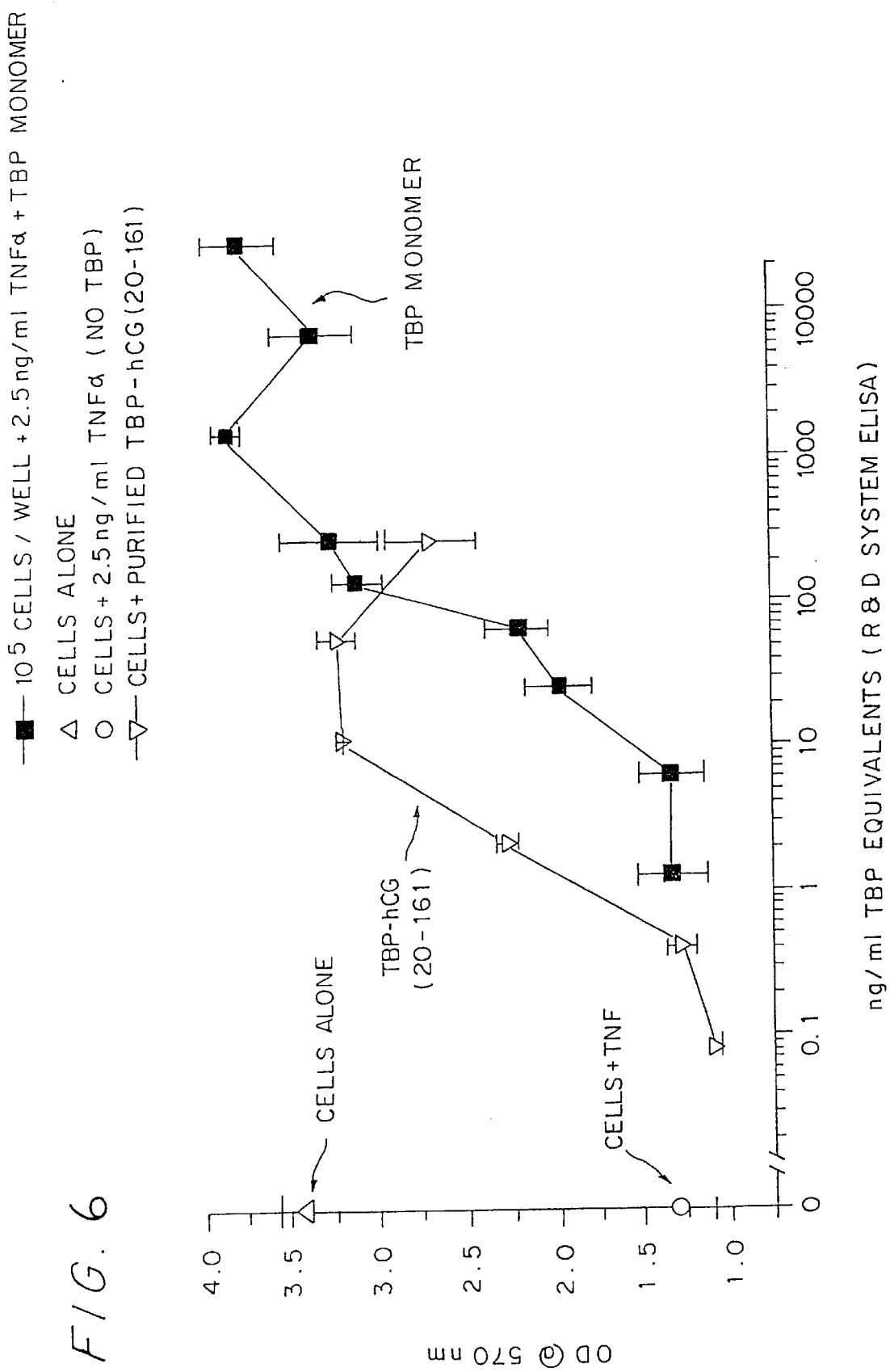
FIG. 6 is a graph illustrating the dose dependent protective effect of affinity purified CHO cell expressed TBP-hCG (20-161) on TNFα-induced cytotoxicity on BT-20 cells and various controls.

As illustrated in FIGS. 4–6 (points on y-axis), addition of TNF (2.5 ng/ml) results in a clear reduction in live cell number (as assessed by OD 570). In every case, active samples have as a maximal protective effect the restoration of cell viability to the level seen in the absence of added TNF (i.e., the control labeled "cells alone").

The positive controls, r-hTBP-1 and TBP-IgG3, are both protective, showing a clear dose-dependence and ED50s of approximately 100 ng/ml for the r-hTBP-1 (FIGS. 4–6) and about 1.5 ng/ml for TBP-IgG3 (FIG. 4) respectively.

The TBP-hCG constructs from 1x media (CHO or COS) or from the immunopurification show dose-dependent protection, with approximate ED50s ranging from 2–11 ng/ml (FIGS. 4–6).

The results from the in vitro bioassay are reported in Table 5. The data indicate that the hybrid proteins inhibit TNF cytotoxicity, and that they are substantially more potent than the TBP monomer. The negative controls were devoid of protective activity.

TABLE 5

Preliminary Assessment of the hybrid proteins in TNF Cytotoxicity Assay

| Construct | Fusion partner | Anti-TNF activity (ED50) in BT-20 bioassay** |
|---|---|---|
| r-hTBP-1 | none | 100 ng/ml |
| TBP-IgG3 | IgG3 heavy chain constant region | 1.5 ng/ml |
| TBP(20-161)-hCG | hCGα and hCGβ (heterodimer) | 2 ng/ml |
| TBP(20-190)-hCG | hCGα and hCGβ (heterodimer) | 8–11 ng/ml |

**The quantitation of material for dosing and estimation of ED50 was made using the TBP ELISA.

In addition to the possibility that dimerization of TBP may increase potency, it is also possible that the activity of the hybrid proteins are not related to dimeric interaction with TBP, but rather to steric inhibition due to the partner of the hybrid interfering with soluble TBP/TNF binding to cell-surface TNF receptors.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Smith, R. A. et al., J. Biol. Chem. 262:6951–6954, 1987.
2. Eck, M. J. et al., J. Biol. Chem. 264:17595–17605, 1989.
3. Jones, E. Y. et al, Nature 338:225–228, 1989.
4. Eck, M. J. et al., J. Biol. Chem. 267:2119–2122, 1992.
5. Pierce, J. G. et al., Annu. Rev. Biochem. 50:465–495, 1981.
6. Lapthorn, A. J. et al., Nature 369:455–461, 1994.
7. Wu, H., et al., Structure 2:545–550, 1994.
8. Engelmann, H., et al., J. Biol. Chem. 265:14497–14504, 1990.
9. Adam, D. et al., J. Biol. Chem. 270:17482–17487, 1995.
10. Loetscher, H. R., et al., J. Biol. Chem. 266:18324–18329, 1991.

11. Banner, D. W., et al., Cell 73:431–445, 1993.

12. Pennica, D., et al., Biochemistry 32:3131–3138, 1993.

13. Engelmann, H. et al., J. Biol. Chem. 265:1531–1536, 1990.

14. Van Zee, K. J. et al., Proc. Natl. Acad. Sci. USA 89:4845–4849, 1992.

15. Aderka, D. et al., J. Exp. Med. 175:323–329, 1992.

16. Mohler, K. M., et al., J. Immunol. 151:1548–1561, 1993.

17. Bertini, R., et al., Eur. Cytokine Netw., 1993.

18. Piguet, P. F., et al., Immunology 77:510–514, 1992.

19. Williams, R. O., et al., Immunology 84:433–439, 1995.

20. Capon, D. J., et al., Nature 337: 525–531, 1989.

21. Ashkenazi, A., et al., Proc. Natl. Acad. Sci. 88:10535–10539, 1991.

22. Suitters, A. J., et al. J. Exp. Med. 179:849–856, 1994.

23. Nolan, O. et al., Biochim. Biophys. Acta 1040:1–11, 1990.

24. Rodrigues, M. L., et al., J. Immunol. 151:6954–6961, 1993.

25. Chang, H.-C., et al., Proc. Natl. Acad. Sci. USA 91:11408–11412, 1994.

26. Wu, Z., et al., J. Biol. Chem. 270:16039–16044, 1995.

27. Bazzoni, F. et al, Proc. Natl. Acad. Sci. USA 92:5376–5380, 1995.

28. Boldin, M. P., et al., J. Biol. Chem. 270:387–391, 1995.

29. Vu, T.-K. H., et al., Cell, 64:1057–1068, 1991.

30. Song, H. Y., et al., J. Biol. Chem. 269:22492–22495, 1994.

31. Russell, D. A., et al., J. Infectious Diseases 171:1528–1538, 1995.

32. Rao C. V. et al., Am. J. Obstet. Gynecol., 146, 65–68, 1983.

33. Damewood M. D. et al., Fertil. Steril. 52, 398–400, 1989.

34. Chen, F., et al., Mol. Endocrinol. 6:914–919, 1992.

35. Bielinska, M., et al., J. Cell Biol. 111:330a, 1990.

36. Furuhashi, M., et al., Mol Endocrinol. 9:54–63, 1995.

37. Sugahara, T., et al., Proc. Natl. Acad. Sci. USA 92:2041–2045, 1995.

38. Johnson, G. A., et al., Biol. Reprod. 52:68–73, 1995.

39. Urlaub, G. and Chasin, L. Proc. Natl. Acad. Sci. USA 77:4216–4220, 1980.

40. Nophar, Y., et al., EMBO J. 9:3269–3278, 1990.

41. Fiddes, J. C. et al., Nature 281:351–356, 1979.

42. Fiddes, J. C. et al., Nature 286:684–687, 1980.

43. Elion, E. A., in Current Protocols in Molecular Biology, eds. Ausuble, FM. et al., John Wiley & Sons, 1993.

44. Campbell, R., Proc. Natl. Acad. Sci. USA 88:760–764, 1991.

45. Cole E. S. et al., Biotechnology, 11, 1014–1024, 1993.

46. Gluzman, Y., Cell 23:175–182, 1981.

47. Chu, G. et al., Nucl. Acid Res. 15:1311–1326, 1987.

48. Yen, J. et al., J. Immunotherapy 10:174–181, 1991.

---

What is claimed is:

1. A hybrid protein comprising two different coexpressed amino acid sequences forming a heterodimer, each comprising:
   (a) at least one amino acid sequence selected from the group consisting of a chain of a homomeric receptor, a chain of a heteromeric receptor, a ligand other than a gonadotropin, a fragment of said chain of said homomeric receptor, said chain of said heteromeric receptor, or said ligand, wherein said ligand or fragment thereof retains ligand-receptor binding capability and said chain of said homomeric receptor or fragment thereof, and said chain of said heteromeric receptor or fragment thereof retain ligand-receptor binding capability either alone or in association with a homologous or heterologous chain of said receptor; and
   (b) a subunit of a heterodimeric proteinaceous hormone, or a fragment thereof which retains the ability of the subunit to form a heterodimer with other subunits thereof;
   wherein sequences (a) and (b) are joined either directly or through a peptide linker, and in which the sequences (b) in each of said two coexpressed sequences aggregate with each other to dimerize and form a heterodimer.

2. A hybrid protein in accordance with claim 1, wherein said sequence (a) is selected from the group consisting of TNF Binding Protein 1 (TBP1), TNF Binding Protein 2 (TBP2) or a fragment of said TBP1 or TBP2 still containing the ligand binding domain; the extracellular domain of the IFNα/β receptor or the IFNγ receptor; a gonadotropin receptor or extracellular fragments thereof; and IL-6, IFN-β, thrombopoietin (TPO) or fragments thereof.

3. A hybrid protein in accordance with claim 1, wherein said sequence (b) is selected from the group consisting of subunits of hCG, FSH, LH, TSH or inhibin, and fragments thereof.

4. A hybrid protein in accordance with claim 1, wherein sequence (a) is joined, either directly or via a linker, to the amino terminus of sequence (b).

5. A hybrid protein in accordance with claim 1, wherein sequence (a) is joined, either directly or via a linker, to the carboxy terminus of sequence (b).

6. A hybrid protein in accordance with claim 1, wherein said two coexpressed amino acid sequences each include the sequence for TBP1 or a fragment thereof having amino acid residues 20–161 or 20–190 of TBP1, as sequence (a) and the respective α and β subunits of hCG or fragments thereof, as sequence (b), wherein said two coexpressed amino acid sequences form a heterodimer through association of said α and β subunits of hCG or fragments thereof.

7. A hybrid protein in accordance with claim 1, wherein said two coexpressed amino acid sequences each include the extracellular domain of a gonadotropin receptor as sequence (a) and the respective α and β subunits of a gonadotropin as sequence (b).

8. A hybrid protein in accordance with claim 7, wherein said sequence (a) is the FSH receptor extracellular domain and sequence (b) is a subunit of FSH.

9. A hybrid protein in accordance with claim 7, wherein said sequences (a) and (b) are linked with a peptide linker.

10. A hybrid protein in accordance with claim 9, wherein said peptide linker has an enzyme cleavage site.

11. A hybrid protein in accordance with claim 10, wherein said enzyme cleavage site is a thrombin cleavage site.

12. A hybrid protein in accordance with claim 10, wherein said enzyme cleavage site is recognized and cleaved by an enzyme which is found in the ovary.

13. A hybrid protein in accordance with claim 9, wherein said peptide linker serves as a flexible hinge.

14. A pharmaceutical composition comprising a hybrid protein in accordance with claim 1 and a pharmaceutically acceptable carrier and/or excipient.

15. The hybrid protein of claim 1, wherein each of said two coexpressed amino acid sequences forming a heterodimer consists essentially of sequences (a) and (b).

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 1049 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 278..1047

(xi) SEQUENCE DESCRIPTION: SEQ ID NO:1:

```
TCCACATGGC TACAGGTAAG CGCCCCTAAA ATCCCTTTGG GCACAATGTG TCCTGAGGGG        60

AGAGGCAGCG ACCTGTAGAT GGGACGGGGG CACTAACCCT CAGGTTTGGG GCTTCTCAAT       120

CTCACTATCG CCATGTAAGC CCAGTATTTG GCCAATCTCA GAAAGCTCCT CCTCCCTGGA       180

GGGATGGAGA GAGAAAAACA AACAGCTCCT GGAGCAGGGA GAGTGCTGGC CTCTTGCTCT       240

CCGGCTCCCT CTGTTGCCCT CTGGTTTCTC CCCAGGC TCC CGG ACG TCC CTG CTC       295
                                        Ser Arg Thr Ser Leu Leu
                                         1               5

CTG GCT TTT GGC CTG CTC TGC CTG CCC TGG CTT CAA GAG GGC AGT GCC        343
Leu Ala Phe Gly Leu Leu Cys Leu Pro Trp Leu Gln Glu Gly Ser Ala
         10               15              20
```

```
GAT AGT GTG TGT CCC CAA GGA AAA TAT ATC CAC CCT CAA AAT AAT TCC            391
Asp Ser Val Cys Pro Gln Gly Lys Tyr Ile His Pro Gln Asn Asn Ser
        25                  30                  35

ATT TGC TGT ACC AAG TGC CAC AAA GGA ACC TAC TTG TAC AAT GAC TGT            439
Ile Cys Cys Thr Lys Cys His Lys Gly Thr Tyr Leu Tyr Asn Asp Cys
        40                  45                  50

CCA GGC CCG GGG CAG GAT ACG GAC TGC AGG GAG TGT GAG AGC GGC TCC            487
Pro Gly Pro Gly Gln Asp Thr Asp Cys Arg Glu Cys Glu Ser Gly Ser
55                      60                  65                  70

TTC ACC GCT TCA GAA AAC CAC CTC AGA CAC TGC CTC AGC TGC TCC AAA            535
Phe Thr Ala Ser Glu Asn His Leu Arg His Cys Leu Ser Cys Ser Lys
                    75                  80                  85

TGC CGA AAG GAA ATG GGT CAG GTG GAG ATC TCT TCT TGC ACA GTG GAC            583
Cys Arg Lys Glu Met Gly Gln Val Glu Ile Ser Ser Cys Thr Val Asp
                90                  95                  100

CGG GAC ACC GTG TGT GGC TGC AGG AAG AAC CAG TAC CGG CAT TAT TGG            631
Arg Asp Thr Val Cys Gly Cys Arg Lys Asn Gln Tyr Arg His Tyr Trp
            105                 110                 115

AGT GAA AAC CTT TTC CAG TGC TTC AAT TGC AGC CTC TGC CTC AAT GGG            679
Ser Glu Asn Leu Phe Gln Cys Phe Asn Cys Ser Leu Cys Leu Asn Gly
        120                 125                 130

ACC GTG CAC CTC TCC TGC CAG GAG AAA CAG AAC ACC GTG TGC ACC TGC            727
Thr Val His Leu Ser Cys Gln Glu Lys Gln Asn Thr Val Cys Thr Cys
135                 140                 145                 150

CAT GCA GGT TTC TTT CTA AGA GAA AAC GAG TGT GTC TCC TGT GCC GGT            775
His Ala Gly Phe Phe Leu Arg Glu Asn Glu Cys Val Ser Cys Ala Gly
                155                 160                 165

GCT GCC CCA GGT TGC CCA GAA TGC ACG CTA CAG GAA AAC CCA TTC TTC            823
Ala Ala Pro Gly Cys Pro Glu Cys Thr Leu Gln Glu Asn Pro Phe Phe
            170                 175                 180

TCC CAG CCG GGT GCC CCA ATA CTT CAG TGC ATG GGC TGC TGC TTC TCT            871
Ser Gln Pro Gly Ala Pro Ile Leu Gln Cys Met Gly Cys Cys Phe Ser
        185                 190                 195

AGA GCA TAT CCC ACT CCA CTA AGG TCC AAG AAG ACG ATG TTG GTC CAA            919
Arg Ala Tyr Pro Thr Pro Leu Arg Ser Lys Lys Thr Met Leu Val Gln
200                 205                 210

AAG AAC GTC ACC TCA GAG TCC ACT TGC TGT GTA GCT AAA TCA TAT AAC            967
Lys Asn Val Thr Ser Glu Ser Thr Cys Cys Val Ala Lys Ser Tyr Asn
215                 220                 225                 230

AGG GTC ACA GTC ATG GGG GGT TTC AAA GTG GAG AAC CAC ACG GGG TGC           1015
Arg Val Thr Val Met Gly Gly Phe Lys Val Glu Asn His Thr Gly Cys
                235                 240                 245

CAC TGC AGT ACT TGT TAT TAT CAC AAA TCT   TA AG                           1049
His Cys Ser Thr Cys Tyr Tyr His Lys Ser
            250                 255

(2) INFORMATION FOR SEQ ID NO:2:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO:2:

Ser Arg Thr Ser Leu Leu Leu Ala Phe Gly Leu Leu Cys Leu Pro Trp
1               5                   10                  15

Leu Gln Glu Gly Ser Ala Asp Ser Val Cys Pro Gln Gly Lys Tyr Ile
            20                  25                  30
```

```
His Pro Gln Asn Asn Ser Ile Cys Cys Thr Lys Cys His Lys Gly Thr
         35                  40                  45

Tyr Leu Tyr Asn Asp Cys Pro Gly Pro Gly Gln Asp Thr Asp Cys Arg
     50                  55                  60

Glu Cys Glu Ser Gly Ser Phe Thr Ala Ser Glu Asn His Leu Arg His
 65                  70                  75                  80

Cys Leu Ser Cys Ser Lys Cys Arg Lys Glu Met Gly Gln Val Glu Ile
                 85                  90                  95

Ser Ser Cys Thr Val Asp Arg Asp Thr Val Cys Gly Cys Arg Lys Asn
             100                 105                 110

Gln Tyr Arg His Tyr Trp Ser Glu Asn Leu Phe Gln Cys Phe Asn Cys
         115                 120                 125

Ser Leu Cys Leu Asn Gly Thr Val His Leu Ser Cys Gln Glu Lys Gln
     130                 135                 140

Asn Thr Val Cys Thr Cys His Ala Gly Phe Phe Leu Arg Glu Asn Glu
145                 150                 155                 160

Cys Val Ser Cys Ala Gly Ala Ala Pro Gly Cys Pro Glu Cys Thr Leu
                 165                 170                 175

Gln Glu Asn Pro Phe Phe Ser Gln Pro Gly Ala Pro Ile Leu Gln Cys
             180                 185                 190

Met Gly Cys Cys Phe Ser Arg Ala Tyr Pro Thr Pro Leu Arg Ser Lys
         195                 200                 205

Lys Thr Met Leu Val Gln Lys Asn Val Thr Ser Glu Ser Thr Cys Cys
     210                 215                 220

Val Ala Lys Ser Tyr Asn Arg Val Thr Val Met Gly Gly Phe Lys Val
225                 230                 235                 240

Glu Asn His Thr Gly Cys His Cys Ser Thr Cys Tyr Tyr His Lys Ser
                 245                 250                 255

(2) INFORMATION FOR SEQ ID NO:3:

(i) SEQUENCE CHARACTERISTICS:
        (A) LENGTH: 1202 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 279..1199

(xi) SEQUENCE DESCRIPTION: SEQ ID NO:3:

CTCGAGATGG CTACAGGTAA GCGCCCCTAA AATCCCTTTG GCACAATGT GTCCTGAGGG      60

GAGAGGTAGC GACCTGTAGA TGGGACGGGG GCACTAACCC TGAGGTTTGG GGCTTCTGAA    120

TGTGAGTATC GCCATGTAAG CCCAGTATTT GGCCAATGTC AGAAAGCTCC TGGTCCCTGG    180

AGGGATGGAG AGAGAAAAAC AAACAGCTCC TGGAGCAGGG AGAGTGCTGG CCTCTTGCTC    240

TCCGGCTCCC TCTGTTGCCC TGTGGTTTCT CCCCAGGC TCC CGG ACG TCC CTG        293
                                          Ser Arg Thr Ser Leu
                                                          260

CTC CTG GCT TTT GGC CTG CTC TGC CTG CCC TGG CTT CAA GAG GGC AGT      341
Leu Leu Ala Phe Gly Leu Leu Cys Leu Pro Trp Leu Gln Glu Gly Ser
            265                 270                 275

GCC GAT AGT GTG TGT CCC CAA GGA AAA TAT ATC CAC CCT CAA AAT AAT      389
Ala Asp Ser Val Cys Pro Gln Gly Lys Tyr Ile His Pro Gln Asn Asn
        280                 285                 290
```

```
TCG ATT TGC TGT ACC AAG TGC CAC AAA GGA ACC TAC TTG TAC AAT GAC        437
Ser Ile Cys Cys Thr Lys Cys His Lys Gly Thr Tyr Leu Tyr Asn Asp
    295                 300                 305

TGT CCA GGC CCG GGG CAG GAT ACG GAC TGC AGG GAG TGT GAG AGC GGC        485
Cys Pro Gly Pro Gly Gln Asp Thr Asp Cys Arg Glu Cys Glu Ser Gly
310                 315                 320                 325

TCT TTC ACC GCT TCA GAA AAC CAC CTC AGA CAC TGC CTC AGC TGC TCC        533
Ser Phe Thr Ala Ser Glu Asn His Leu Arg His Cys Leu Ser Cys Ser
                330                 335                 340

AAA TGC CGA AAG GAA ATG GGT CAG GTG GAG ATC TCT TCT TGC ACA GTG        581
Lys Cys Arg Lys Glu Met Gly Gln Val Glu Ile Ser Ser Cys Thr Val
            345                 350                 355

GAC CGG GAC ACC GTG TGT GGC TGC AGG AAG AAC CAG TAC CGG CAT TAT        629
Asp Arg Asp Thr Val Cys Gly Cys Arg Lys Asn Gln Tyr Arg His Tyr
                360                 365                 370

TGG AGT GAA AAC CTT TTC CAG TGC TTC AAT TGC AGC CTC TGC CTC AAT        677
Trp Ser Glu Asn Leu Phe Gln Cys Phe Asn Cys Ser Leu Cys Leu Asn
    375                 380                 385

GGG ACC GTG CAC CTC TCC TGC CAG GAG AAA CAG AAC ACC GTG TGC ACC        725
Gly Thr Val His Leu Ser Cys Gln Glu Lys Gln Asn Thr Val Cys Thr
390                 395                 400                 405

TGC CAT GCA GGT TTC TTT CTA AGA GAA AAC GAG TGT GTC TCC TGT GCT        773
Cys His Ala Gly Phe Phe Leu Arg Glu Asn Glu Cys Val Ser Cys Ala
                410                 415                 420

GGT GCT GGT CCA CGG TGC CGC CCC ATC AAT GCC ACC CTG GCT GTG GAG        821
Gly Ala Gly Pro Arg Cys Arg Pro Ile Asn Ala Thr Leu Ala Val Glu
            425                 430                 435

AAG GAG GGC TGC CCC GTG TGC ATC ACC GTC AAC ACC ACC ATC TGT GCC        869
Lys Glu Gly Cys Pro Val Cys Ile Thr Val Asn Thr Thr Ile Cys Ala
                440                 445                 450

GGC TAC TGC CCC ACC ATG ACC CGC GTG CTG CAG GGG GTC CTC CCC GCC        917
Gly Tyr Cys Pro Thr Met Thr Arg Val Leu Gln Gly Val Leu Pro Ala
    455                 460                 465

CTG CCT CAG GTG GTG TGC AAC TAC CGC GAT GTG CGC TTC GAG TCC ATC        965
Leu Pro Gln Val Val Cys Asn Tyr Arg Asp Val Arg Phe Glu Ser Ile
470                 475                 480                 485

CGG CTC CCT GGC TGC CCG CGC GGC GTG AAC CCC GTG GTC TCC TAC GCT       1013
Arg Leu Pro Gly Cys Pro Arg Gly Val Asn Pro Val Val Ser Tyr Ala
                490                 495                 500

GTG GCT CTC AGC TGT CAA TGT GCA CTC TGC CGC CGC AGC ACC ACT GAC       1061
Val Ala Leu Ser Cys Gln Cys Ala Leu Cys Arg Arg Ser Thr Thr Asp
            505                 510                 515

TGC GGG GGT CCC AAG GAC CAC CCC TTG ACC TGT GAT GAC CCC CGC TTC       1109
Cys Gly Gly Pro Lys Asp His Pro Leu Thr Cys Asp Asp Pro Arg Phe
                520                 525                 530

CAG GAC TCC TCT TCC TCA AAG GCC CCT CCC CCC AGC CTT CCA AGC CCA       1157
Gln Asp Ser Ser Ser Ser Lys Ala Pro Pro Pro Ser Leu Pro Ser Pro
    535                 540                 545

TCC CGA CTC CCG GGG CCC TCG GAC ACC CCG ATC CTC CCA CAA TAA           1202
Ser Arg Leu Pro Gly Pro Ser Asp Thr Pro Ile Leu Pro Gln
550                 555                 560
```

(2) INFORMATION FOR SEQ ID NO:4:

(i) SEQUENCE CHARACTERISTICS:
        (A) LENGTH: 307 amino acids
        (B) TYPE: amino acid
        (D) TOPOLOGY: linear (ii) MOLECULE TYPE: protein (xi) SEQUENCE DESCRIPTION: SEQ ID NO:4:

```
Ser Arg Thr Ser Leu Leu Leu Ala Phe Gly Leu Leu Cys Leu Pro Trp
  1               5                  10                  15

Leu Gln Glu Gly Ser Ala Asp Ser Val Cys Pro Gln Gly Lys Tyr Ile
             20                  25                  30

His Pro Gln Asn Asn Ser Ile Cys Cys Thr Lys Cys His Lys Gly Thr
             35                  40                  45

Tyr Leu Tyr Asn Asp Cys Pro Gly Pro Gly Gln Asp Thr Asp Cys Arg
         50                  55                  60

Glu Cys Glu Ser Gly Ser Phe Thr Ala Ser Glu Asn His Leu Arg His
 65                  70                  75                  80

Cys Leu Ser Cys Ser Lys Cys Arg Lys Glu Met Gly Gln Val Glu Ile
                 85                  90                  95

Ser Ser Cys Thr Val Asp Arg Asp Thr Val Cys Gly Cys Arg Lys Asn
                100                 105                 110

Gln Tyr Arg His Tyr Trp Ser Glu Asn Leu Phe Gln Cys Phe Asn Cys
            115                 120                 125

Ser Leu Cys Leu Asn Gly Thr Val His Leu Ser Cys Gln Glu Lys Gln
        130                 135                 140

Asn Thr Val Cys Thr Cys His Ala Gly Phe Phe Leu Arg Glu Asn Glu
145                 150                 155                 160

Cys Val Ser Cys Ala Gly Ala Gly Pro Arg Cys Arg Pro Ile Asn Ala
                165                 170                 175

Thr Leu Ala Val Glu Lys Glu Gly Cys Pro Val Cys Ile Thr Val Asn
                180                 185                 190

Thr Thr Ile Cys Ala Gly Tyr Cys Pro Thr Met Thr Arg Val Leu Gln
            195                 200                 205

Gly Val Leu Pro Ala Leu Pro Gln Val Val Cys Asn Tyr Arg Asp Val
        210                 215                 220

Arg Phe Glu Ser Ile Arg Leu Pro Gly Cys Pro Arg Gly Val Asn Pro
225                 230                 235                 240

Val Val Ser Tyr Ala Val Ala Leu Ser Cys Gln Cys Ala Leu Cys Arg
                245                 250                 255

Arg Ser Thr Thr Asp Cys Gly Gly Pro Lys Asp His Pro Leu Thr Cys
            260                 265                 270

Asp Asp Pro Arg Phe Gln Asp Ser Ser Ser Lys Ala Pro Pro Pro
            275                 280                 285

Ser Leu Pro Ser Pro Ser Arg Leu Pro Gly Pro Ser Asp Thr Pro Ile
        290                 295                 300

Leu Pro Gln
305
```

(2) INFORMATION FOR SEQ ID NO:5:

(i) SEQUENCE CHARACTERISTICS:
        (A) LENGTH: 1147 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 278..1132

(xi) SEQUENCE DESCRIPTION: SEQ ID NO:5:

TCGAGATGGC TACAGGTAAG CGCCCCTAAA ATCCCTTTGG GCACAATGTG TCCTGAGGGG    60

```
AGAGGCAGCG ACCTGTAGAT GGGACGGGGG CACTAACCCT CAGGTTTGGG GCTTTTGAAT      120

GTGAGTATGG CCATGTAAGC CCAGTATTTG CCCAATCTCA GAAAGCTCCT GGTCCCTGGA      180

GGGATGGAGA GAGAAAAACA AACAGCTCCT GGAGCAGGGA CACTCCTGGC CTCTTGCTCT      240

GCGGCTCCGT GTGTTGCCCT GTGGTTTCTC CCCACGC TCC CGG ACG TCC CTG CTC      295
                                         Ser Arg Thr Ser Leu Leu
                                                         310

CTG GCT TTT GGC CTG CTC TGC CTG CCC TGG CTT CAA GAG GGT AGT GCC      343
Leu Ala Phe Gly Leu Leu Cys Leu Pro Trp Leu Gln Glu Gly Ser Ala
        315                 320                 325

GAT AGT GTG TGT CCC CAA GGA AAA TAT ATC CAC CCT CAA AAT AAT TCG      391
Asp Ser Val Cys Pro Gln Gly Lys Tyr Ile His Pro Gln Asn Asn Ser
330                 335                 340                 345

ATT TGC TGT ACC AAG TGC CAC AAA GGA ACC TAC TTG TAC AAT GAC TGT      439
Ile Cys Cys Thr Lys Cys His Lys Gly Thr Tyr Leu Tyr Asn Asp Cys
                350                 355                 360

CCA GGC CCG GGG CAG GAT ACC GAC TGC AGG GAG TGT GAG AGC GGC TCC      487
Pro Gly Pro Gly Gln Asp Thr Asp Cys Arg Glu Cys Glu Ser Gly Ser
            365                 370                 375

TTC ACC GCT TCA GAA AAC CAC CTC AGA CAC TGC CTC AGC TGC TCC AAA      535
Phe Thr Ala Ser Glu Asn His Leu Arg His Cys Leu Ser Cys Ser Lys
        380                 385                 390

TGC CGA AAG GAA ATG GGT CAG GTG GAG ATC TCT TCT TGC ACA GTG GAC      583
Cys Arg Lys Glu Met Gly Gln Val Glu Ile Ser Ser Cys Thr Val Asp
    395                 400                 405

CGG GAC ACC GTG TGT GGC TGC AGG AAG AAC CAG TAC CGG CAT TAT TGG      631
Arg Asp Thr Val Cys Gly Cys Arg Lys Asn Gln Tyr Arg His Tyr Trp
410                 415                 420                 425

AGT GAA AAC CTT TTC CAG TGC TTC AAT TGC ACC CTC TGC CTC AAT GGG      679
Ser Glu Asn Leu Phe Gln Cys Phe Asn Cys Thr Leu Cys Leu Asn Gly
                430                 435                 440

ACC GTG CAC CTC TCC TGT CAG GAG AAA CAG AAC ACC GTC TGC ACC TGC      727
Thr Val His Leu Ser Cys Gln Glu Lys Gln Asn Thr Val Cys Thr Cys
            445                 450                 455

CAT GCA GGT TTC TTT CTA AGA GAA AAC GAG TGT GTC TCC TGT AGT AAC      775
His Ala Gly Phe Phe Leu Arg Glu Asn Glu Cys Val Ser Cys Ser Asn
        460                 465                 470

TGT AAG AAA AGC CTG GAG TGC ACG AAG TTG TCC CTA CCC CAG ATT GAG      823
Cys Lys Lys Ser Leu Glu Cys Thr Lys Leu Ser Leu Pro Gln Ile Glu
    475                 480                 485

AAT GTT AAG GGC ACT GAG GAC TCA GGC ACC ACA GCC GGT GCT GCC CCA      871
Asn Val Lys Gly Thr Glu Asp Ser Gly Thr Thr Ala Gly Ala Ala Pro
490                 495                 500                 505

GGT TGC CCA GAA TGC ACG CTA CAG GAA AAC CCA TTC TTC TCC CAG CCG      919
Gly Cys Pro Glu Cys Thr Leu Gln Glu Asn Pro Phe Phe Ser Gln Pro
                510                 515                 520

GGT GCC CCA ATA CTT CAG TGC ATG GGC TGC TGC TTC TCT AGA GCA TAT      967
Gly Ala Pro Ile Leu Gln Cys Met Gly Cys Cys Phe Ser Arg Ala Tyr
            525                 530                 535

CCC ACT CCA CTA AGG TCC AAG AAG ACG ATG TTG GTC CAA AAG AAC GTC     1015
Pro Thr Pro Leu Arg Ser Lys Lys Thr Met Leu Val Gln Lys Asn Val
        540                 545                 550

ACC TCA GAG TCC ACT TGC TGT GTA GCT AAA TCA TAT AAC AGG GTC ACA     1063
Thr Ser Glu Ser Thr Cys Cys Val Ala Lys Ser Tyr Asn Arg Val Thr
    555                 560                 565

GTA ATG GGG GGT TTC AAA GTG GAG AAC CAC ACG GCG TGC CAC TGC AGT     1111
Val Met Gly Gly Phe Lys Val Glu Asn His Thr Ala Cys His Cys Ser
570                 575                 580                 585
```

```
ACT TGT TAT TAT CAC AAA TCT TAAGGATCCC TCGAG                                    1147
Thr Cys Tyr Tyr His Lys Ser
            590
```

(2) INFORMATION FOR SEQ ID NO:6:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO:6:

```
Ser Arg Thr Ser Leu Leu Leu Ala Phe Gly Leu Leu Cys Leu Pro Trp
 1               5                  10                  15

Leu Gln Glu Gly Ser Ala Asp Ser Val Cys Pro Gln Gly Lys Tyr Ile
                20                  25                  30

His Pro Gln Asn Asn Ser Ile Cys Cys Thr Lys Cys His Lys Gly Thr
            35                  40                  45

Tyr Leu Tyr Asn Asp Cys Pro Gly Pro Gly Gln Asp Thr Asp Cys Arg
        50                  55                  60

Glu Cys Glu Ser Gly Ser Phe Thr Ala Ser Glu Asn His Leu Arg His
65                  70                  75                  80

Cys Leu Ser Cys Ser Lys Cys Arg Lys Glu Met Gly Gln Val Glu Ile
                85                  90                  95

Ser Ser Cys Thr Val Asp Arg Asp Thr Val Cys Gly Cys Arg Lys Asn
                100                 105                 110

Gln Tyr Arg His Tyr Trp Ser Glu Asn Leu Phe Gln Cys Phe Asn Cys
            115                 120                 125

Thr Leu Cys Leu Asn Gly Thr Val His Leu Ser Cys Gln Glu Lys Gln
130                 135                 140

Asn Thr Val Cys Thr Cys His Ala Gly Phe Phe Leu Arg Glu Asn Glu
145                 150                 155                 160

Cys Val Ser Cys Ser Asn Cys Lys Lys Ser Leu Glu Cys Thr Lys Leu
                165                 170                 175

Ser Leu Pro Gln Ile Glu Asn Val Lys Gly Thr Glu Asp Ser Gly Thr
                180                 185                 190

Thr Ala Gly Ala Ala Pro Gly Cys Pro Glu Cys Thr Leu Gln Glu Asn
            195                 200                 205

Pro Phe Phe Ser Gln Pro Gly Ala Pro Ile Leu Gln Cys Met Gly Cys
        210                 215                 220

Cys Phe Ser Arg Ala Tyr Pro Thr Pro Leu Arg Ser Lys Lys Thr Met
225                 230                 235                 240

Leu Val Gln Lys Asn Val Thr Ser Glu Ser Thr Cys Cys Val Ala Lys
                245                 250                 255

Ser Tyr Asn Arg Val Thr Val Met Gly Gly Phe Lys Val Glu Asn His
                260                 265                 270

Thr Ala Cys His Cys Ser Thr Cys Tyr Tyr His Lys Ser
            275                 280                 285
```

(2) INFORMATION FOR SEQ ID NO:7:

(i) SEQUENCE CHARACTERISTICS:
        (A) LENGTH: 1301 base pairs
        (B) TYPE: nucleic acid
        (C) STRANDEDNESS: single
        (D) TOPOLOGY: linear -continued (ii) MOLECULE TYPE: cDNA (ix) FEATURE:
    (A) NAME/KEY: CDS
    (B) LOCATION: 279..1287

(xi) SEQUENCE DESCRIPTION: SEQ ID NO:7:

```
CTCGAGATGG CTACAGGTAA GCGCCCCTAA AATCCCTTTG GGCACAATGT GTCCTGAGGG        60

GAGAGGCAGC GACCTGTAGA TGGGACGGGG GCACTAACCC TCAGGTTTGG GGCTTCTGAA       120

TGTGAGTATC GCCATGTAAG CCCAGTATTT GGCCAATGTC AGAAAGCTCC TGGTCCCTGG       180

AGGGATGGAG AGAGAAAAAC AAACACCTCC TGGAGCAGGG AGAGTGCTGC CCTCTTGCTC       240

TCCGGCTCCC TCTGTTGCCC TCTGGTTTCT CCCCAGGC TCC CGG ACG TCC CTG           293
                                          Ser Arg Thr Ser Leu
                                                          290

CTC CTG GCT TTT GGC CTG CTC TGC CTG CCC TGG CTT CAA GAG GGC AGT         341
Leu Leu Ala Phe Gly Leu Leu Cys Leu Pro Trp Leu Gln Glu Gly Ser
            295                 300                 305

GCC GAT AGT GTG TGT CCC CAA GGA AAA TAT ATC CAC CCT CAA AAT AAT         389
Ala Asp Ser Val Cys Pro Gln Gly Lys Tyr Ile His Pro Gln Asn Asn
        310                 315                 320

TCG ATT TGC TGT ACC AAG TGC CAC AAA GGA ACC TAC TTG TAC AAT GAC         437
Ser Ile Cys Cys Thr Lys Cys His Lys Gly Thr Tyr Leu Tyr Asn Asp
    325                 330                 335

TGT CCA GGC CCG GGG CAG GAT ACG GAC TGC AGG GAG TGT GAG AGC GGC         485
Cys Pro Gly Pro Gly Gln Asp Thr Asp Cys Arg Glu Cys Glu Ser Gly
340                 345                 350

TCC TTC ACC GCT TCA GAA AAC CAC CTC AGA CAC TGC CTC AGC TGC TCC         533
Ser Phe Thr Ala Ser Glu Asn His Leu Arg His Cys Leu Ser Cys Ser
355                 360                 365                 370

AAA TGC CGA AAG GAA ATG GGT CAG GTG GAG ATC TCT TCT TGC ACA GTG         581
Lys Cys Arg Lys Glu Met Gly Gln Val Glu Ile Ser Ser Cys Thr Val
                375                 380                 385

GAC CGG GAC ACC GTG TGT GGC TGC AGG AAG AAC CAG TAC CGG CAT TAT         629
Asp Arg Asp Thr Val Cys Gly Cys Arg Lys Asn Gln Tyr Arg His Tyr
            390                 395                 400

TGG AGT GAA AAC CTT TTC CAG TGC TTC AAT TGC AGC CTC TGC CTC AAT         677
Trp Ser Glu Asn Leu Phe Gln Cys Phe Asn Cys Ser Leu Cys Leu Asn
        405                 410                 415

GGG ACC GTG CAC CTC TCC TGC CAG GAG AAA CAG AAC ACC GTG TGC ACC         725
Gly Thr Val His Leu Ser Cys Gln Glu Lys Gln Asn Thr Val Cys Thr
    420                 425                 430

TGC CAT GCA GGT TTC TTT CTA AGA GAA AAC GAG TGT GTC TCC TGT AGT         773
Cys His Ala Gly Phe Phe Leu Arg Glu Asn Glu Cys Val Ser Cys Ser
435                 440                 445                 450

AAC TGT AAG AAA AGC CTG GAG TGC ACG AAG TTG TGC CTA CCC CAG ATT         821
Asn Cys Lys Lys Ser Leu Glu Cys Thr Lys Leu Cys Leu Pro Gln Ile
                455                 460                 465

GAG AAT GTT AAG GGC ACT GAG GAC TCA GGC ACC ACA GCT GGT GCT GGT         869
Glu Asn Val Lys Gly Thr Glu Asp Ser Gly Thr Thr Ala Gly Ala Gly
            470                 475                 480

CCA CGG TGC CGC CCC ATC AAT GCC ACC CTG GCT GTG GAG AAG GAG GGC         917
Pro Arg Cys Arg Pro Ile Asn Ala Thr Leu Ala Val Glu Lys Glu Gly
        485                 490                 495

TGC CCC GTG TGC ATC ACC GTC AAC ACC ACC ATC TGT GCC GGC TAC TGC         965
Cys Pro Val Cys Ile Thr Val Asn Thr Thr Ile Cys Ala Gly Tyr Cys
    500                 505                 510

CCC ACC ATG ACC CGC GTG CTG CAG GGG GTC CTG CCG GCC CTG CCT CAG        1013
Pro Thr Met Thr Arg Val Leu Gln Gly Val Leu Pro Ala Leu Pro Gln
515                 520                 525                 530
```

```
GTG GTG TGC AAC TAC CGC GAT GTG CGC TTC GAG TCC ATC CGG CTC CCT    1061
Val Val Cys Asn Tyr Arg Asp Val Arg Phe Glu Ser Ile Arg Leu Pro
                535                 540                 545

GGC TGC CCG CGC GGC GTG AAC CCC GTG GTC TCC TAC GCC GTG GCT CTC    1109
Gly Cys Pro Arg Gly Val Asn Pro Val Val Ser Tyr Ala Val Ala Leu
            550                 555                 560

AGC TGT CAA TGT GCA CTC TGC CGC CGC AGC ACC ACT GAC TGC GGG GGT    1157
Ser Cys Gln Cys Ala Leu Cys Arg Arg Ser Thr Thr Asp Cys Gly Gly
        565                 570                 575

CCC AAG GAC CAC CCC TTG ACC TGT GAT GAC CCC CGC TTC CAG GAC TCC    1205
Pro Lys Asp His Pro Leu Thr Cys Asp Asp Pro Arg Phe Gln Asp Ser
580                 585                 590

TCT TCC TCA AAG GCC CCT CCC CCC AGC CTT CCA AGC CCA TCC CGA CTC    1253
Ser Ser Ser Lys Ala Pro Pro Pro Ser Leu Pro Ser Pro Ser Arg Leu
595                 600                 605                 610

CCG GGG CCC TCG GAC ACC CCG ATC CTC CCA CAA T AAGGATCCCT CGAG      1301
Pro Gly Pro Ser Asp Thr Pro Ile Leu Pro Gln
                615                 620

(2) INFORMATION FOR SEQ ID NO:8:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:8:

Ser Arg Thr Ser Leu Leu Leu Ala Phe Gly Leu Leu Cys Leu Pro Trp
1               5                   10                  15

Leu Gln Glu Gly Ser Ala Asp Ser Val Cys Pro Gln Gly Lys Tyr Ile
            20                  25                  30

His Pro Gln Asn Asn Ser Ile Cys Cys Thr Lys Cys His Lys Gly Thr
        35                  40                  45

Tyr Leu Tyr Asn Asp Cys Pro Gly Pro Gly Gln Asp Thr Asp Cys Arg
    50                  55                  60

Glu Cys Glu Ser Gly Ser Phe Thr Ala Ser Glu Asn His Leu Arg His
65                  70                  75                  80

Cys Leu Ser Cys Ser Lys Cys Arg Lys Glu Met Gly Gln Val Glu Ile
                85                  90                  95

Ser Ser Cys Thr Val Asp Arg Asp Thr Val Cys Gly Cys Arg Lys Asn
            100                 105                 110

Gln Tyr Arg His Tyr Trp Ser Glu Asn Leu Phe Gln Cys Phe Asn Cys
        115                 120                 125

Ser Leu Cys Leu Asn Gly Thr Val His Leu Ser Cys Gln Glu Lys Gln
    130                 135                 140

Asn Thr Val Cys Thr Cys His Ala Gly Phe Phe Leu Arg Glu Asn Glu
145                 150                 155                 160

Cys Val Ser Cys Ser Asn Cys Lys Lys Ser Leu Glu Cys Thr Lys Leu
                165                 170                 175

Cys Leu Pro Gln Ile Glu Asn Val Lys Gly Thr Glu Asp Ser Gly Thr
            180                 185                 190

Thr Ala Gly Ala Gly Pro Arg Cys Arg Pro Ile Asn Ala Thr Leu Ala
        195                 200                 205

Val Glu Lys Glu Gly Cys Pro Val Cys Ile Thr Val Asn Thr Thr Ile
    210                 215                 220
```

```
Cys Ala Gly Tyr Cys Pro Thr Met Thr Arg Val Leu Gln Gly Val Leu
225                 230                 235                 240

Pro Ala Leu Pro Gln Val Val Cys Asn Tyr Arg Asp Val Arg Phe Glu
                245                 250                 255

Ser Ile Arg Leu Pro Gly Cys Pro Arg Gly Val Asn Pro Val Val Ser
            260                 265                 270

Tyr Ala Val Ala Leu Ser Cys Gln Cys Ala Leu Cys Arg Arg Ser Thr
        275                 280                 285

Thr Asp Cys Gly Gly Pro Lys Asp His Pro Leu Thr Cys Asp Asp Pro
    290                 295                 300

Arg Phe Gln Asp Ser Ser Ser Lys Ala Pro Pro Pro Ser Leu Pro
305                 310                 315                 320

Ser Pro Ser Arg Leu Pro Gly Pro Ser Asp Thr Pro Ile Leu Pro Gln
                325                 330                 335
```

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ala Gly Ala Ala Pro Gly
1               5
```

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Ala Gly Ala Gly
1
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
TTTTCTCGAG ATGGCTACAG GTAAGCGCCC                              30
```

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ACCTGGGGCA GCACCGGCAC AGGAGACACA CTCGTTTTC                                    39

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TGTGCCGGTG CTGCCCCAGG TTGCCCAGAA TGCACGCTAC AG                                42

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TTTTGGATCC TTAAGATTTG TGATAATAAC AAGTAC                                      36

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CCGTGGACCA GCACCAGCAC AGGAGACACA CTCGTTTTC                                    39

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TGTGCTGGTG CTGGTCCACG GTGCCGCCCC ATCAAT                                       36

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TTTTGGATCC TTATTGTGGG AGGATCGGGG TG                                           32

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TTTTAGATCT CTTCTTGCAC AGTGGAC                                    27

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TGTGGTGCCT GAGTCCTCAG T                                        21

(2) INFORMATION FOR SEQ ID NO:20:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

ACTGAGGACT CAGGCACCAC AGCCGGTGCT GCCCCAGGTT G                  41

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TTTTTCTAGA GAAGCAGCAG CAGCCCATG                                  29

(2) INFORMATION FOR SEQ ID NO:22:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TTTTCCACAG CCAGGGTGGC ATTGATGGGG CGGCACCGTG GACCAGCACC AGCTGTGGTG    60

CCTGAGTCCT CAGTG                                                                75